United States Patent
Hyde et al.

(10) Patent No.: US 9,757,054 B2
(45) Date of Patent: Sep. 12, 2017

(54) SYSTEMS AND METHODS FOR WARNING OF A PROTRUDING BODY PART OF A WHEELCHAIR OCCUPANT

(71) Applicant: Elwha LLC, Bellevue, WA (US)

(72) Inventors: Roderick A. Hyde, Redmond, WA (US); Jordin T. Kare, Seattle, WA (US); Eric C. Leuthardt, St. Louis, MO (US); Richard T. Lord, Tacoma, WA (US); Robert W. Lord, Seattle, WA (US); Clarence T. Tegreene, Mercer Island, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 99 days.

(21) Appl. No.: 14/015,367

(22) Filed: Aug. 30, 2013

(65) Prior Publication Data
US 2015/0061873 A1 Mar. 5, 2015

(51) Int. Cl.
*A61B 5/11* (2006.01)
*G08B 21/02* (2006.01)
*A61B 5/00* (2006.01)

(52) U.S. Cl.
CPC ........... *A61B 5/1115* (2013.01); *A61B 5/1114* (2013.01); *A61B 5/6894* (2013.01); *A61B 5/746* (2013.01)

(58) Field of Classification Search
None
See application file for complete search history.

(56) References Cited

U.S. PATENT DOCUMENTS

| | | | | |
|---|---|---|---|---|
| 4,284,971 A * | 8/1981 | Lowry | ................. | G08G 1/0175 250/222.1 |
| 4,701,132 A * | 10/1987 | Groesch | ................. | G09B 23/28 434/274 |
| 4,858,622 A * | 8/1989 | Osterweil | ..................... | 600/595 |
| 5,173,692 A * | 12/1992 | Shapiro | .................. | G01S 7/539 340/917 |
| 5,621,290 A * | 4/1997 | Heller | ...................... | B60J 10/00 307/10.1 |
| 6,108,592 A | 8/2000 | Kurtzberg et al. | | |
| 6,177,868 B1 * | 1/2001 | Hollingsworth | ......... | B60Q 9/00 180/271 |
| 6,297,738 B1 | 10/2001 | Newham | | |

(Continued)

FOREIGN PATENT DOCUMENTS

DE  EP1894797  * 3/2008
JP  2009234435 A  * 10/2009

OTHER PUBLICATIONS

Machine Translation of EP1894797.*

*Primary Examiner* — John R Olszewski
*Assistant Examiner* — Navid Ziaeianmehdizadeh
(74) *Attorney, Agent, or Firm* — Foley & Lardner LLP

(57) ABSTRACT

A system for warning of protruding body parts of a medical vehicle occupant includes a sensor, a feedback device, and a processing circuit. The sensor is configured to generate sensor data based on a position of the occupant, and the processing circuit is configured to determine a contour of the medical vehicle, detect a protruding extremity of the occupant based on the sensor data and the contour, and generate a warning using the feedback device, where the warning is based on the detected protruding extremity.

37 Claims, 17 Drawing Sheets

(56) References Cited

U.S. PATENT DOCUMENTS

| | | | |
|---|---|---|---|
| 6,337,549 B1* | 1/2002 | Bledin | E05F 15/46 318/445 |
| 6,842,692 B2 | 1/2005 | Fehr et al. | |
| 6,847,301 B1* | 1/2005 | Olson | 340/666 |
| 6,972,575 B2* | 12/2005 | Lambert | H03K 17/955 318/264 |
| 7,015,666 B2 | 3/2006 | Staus | B60J 10/00 318/286 |
| 7,127,370 B2* | 10/2006 | Kelly et al. | 702/151 |
| 7,204,328 B2 | 4/2007 | LoPresti | |
| 7,426,970 B2 | 9/2008 | Olsen | |
| 7,876,202 B2* | 1/2011 | Liljeblad | B62D 35/001 296/155 |
| 7,940,187 B2 | 5/2011 | Newham | |
| 8,013,722 B2 | 9/2011 | Breuer et al. | |
| 8,203,454 B2 | 6/2012 | Knight et al. | |
| 8,572,891 B2* | 11/2013 | Pribisic | E05F 15/46 49/28 |
| 8,723,677 B1* | 5/2014 | Kiani | 340/573.7 |
| 8,823,529 B2* | 9/2014 | Reed, Jr. | 340/573.4 |
| 8,907,287 B2* | 12/2014 | Vanderpohl | 250/349 |
| 9,000,955 B2* | 4/2015 | Fasshauer | H03K 17/955 341/20 |
| 2003/0024132 A1* | 2/2003 | Kokura | B66F 9/0755 33/712 |
| 2004/0006422 A1 | 1/2004 | Fehr et al. | |
| 2004/0064908 A1* | 4/2004 | Decker | 15/53.2 |
| 2004/0075847 A1 | 4/2004 | McCracken | |
| 2004/0267442 A1 | 12/2004 | Fehr et al. | |
| 2005/0279551 A1 | 12/2005 | LoPresti | |
| 2007/0132597 A1* | 6/2007 | Rodgers | 340/573.1 |
| 2007/0138347 A1 | 6/2007 | Ehlers | |
| 2007/0152427 A1 | 7/2007 | Olsen | |
| 2008/0021731 A1 | 1/2008 | Rodgers | |
| 2008/0059055 A1 | 3/2008 | Geelen et al. | |
| 2008/0180267 A1* | 7/2008 | Kaneko | A61H 3/068 340/686.1 |
| 2009/0121852 A1 | 5/2009 | Breuer et al. | |
| 2009/0278934 A1* | 11/2009 | Ecker | G06K 9/00348 348/152 |
| 2010/0039269 A1* | 2/2010 | Newham | 340/573.4 |
| 2010/0045454 A1* | 2/2010 | Knight et al. | 340/521 |
| 2010/0231376 A1* | 9/2010 | Hirose | 340/517 |
| 2010/0275459 A1* | 11/2010 | Wentworth | F26B 21/004 34/666 |
| 2011/0109577 A1* | 5/2011 | Lee | G06F 3/044 345/173 |
| 2011/0156913 A1* | 6/2011 | Dai | G08B 21/22 340/573.1 |
| 2011/0184642 A1 | 7/2011 | Rotz et al. | |
| 2012/0046821 A1* | 2/2012 | Pettersson et al. | 701/25 |
| 2012/0101402 A1 | 4/2012 | Nguyen | |
| 2013/0222592 A1* | 8/2013 | Gieseke | G08G 1/04 348/148 |
| 2014/0064774 A1* | 3/2014 | Masumoto | G03G 15/5016 399/88 |
| 2014/0204205 A1* | 7/2014 | Kotz | G01B 11/0608 348/142 |
| 2014/0224279 A1* | 8/2014 | Anderson | B60S 3/04 134/18 |

* cited by examiner

SYSTEMS AND METHODS FOR WARNING OF A PROTRUDING BODY PART OF A WHEELCHAIR OCCUPANT

BACKGROUND

Many individuals require the assistance of a wheelchair to be mobile. In general, the wheelchair is manually powered by an occupant or caregiver, or the wheelchair is propelled by motors. In a typical scenario, a nurse may be pushing a patient in a wheelchair throughout a health care facility. In another scenario, the patient may be controlling a motorized wheelchair. As the patient moves about, an extremity may shift to extend beyond the ordinary contour of the wheelchair. However, the nurse may not be aware that the extremity is extending. The patient may also be unaware of the situation or may be unable to physically reposition the extremity. As the wheelchair continues to move, the protruding extremity is vulnerable to collisions with hallways, doorways, and other objects.

SUMMARY

One embodiment relates to a system for warning of protruding body parts of a medical vehicle occupant includes a sensor, a feedback device, and a processing circuit. The sensor is configured to generate sensor data based on a position of the occupant, and the processing circuit is configured to determine a contour of the medical vehicle, detect a protruding extremity of the occupant based on the sensor data and the contour, and generate a warning using the feedback device, wherein the warning is based on the detected protruding extremity.

Another embodiment relates to a method of warning of protruding body parts of a medical vehicle occupant. The method includes generating sensor data with a sensor, wherein the sensor data is based on a position of the occupant; determining a contour of the medical vehicle; detecting a protruding extremity of the occupant based on the sensor data and the contour; and generating a warning using a feedback device, wherein the warning is based on the detected protruding extremity.

Another embodiment relates to a non-transitory computer-readable medium having instructions stored thereon, the instructions forming a program executable by a processing circuit to warn of protruding body parts of a medical vehicle occupant. The instructions include instructions for receiving sensor data from a sensor, wherein the sensor data is based on a position of the occupant; instructions for determining a contour of the medical vehicle; instructions for detecting a protruding extremity of the occupant based on the sensor data and the contour; and instructions for generating a warning using a feedback device, wherein the warning is based on the detected protruding extremity.

Another embodiment relates to a system for updating a navigation system of a medical vehicle, including a sensor and a processing circuit. The sensor is configured to generate sensor data based on a position of the occupant, and the processing circuit is configured to determine a contour of the medical vehicle, detect a protruding extremity of an occupant of the medical vehicle, and notify the navigation system of the medical vehicle of the protruding extremity. Detecting the protruding extremity is based on the sensor data and the contour.

Another embodiment relates to a method of updating a navigation system of a medical vehicle. The method includes generating sensor data with a sensor, wherein the sensor data is based on a position of the occupant, determining a contour of the medical vehicle, detecting a protruding extremity of an occupant of the medical vehicle, and notifying the navigation system of the medical vehicle of the protruding extremity. Detecting the protruding extremity is based on the sensor data and the contour.

Another embodiment relates to a non-transitory computer-readable medium having instructions stored thereon, the instructions forming a program executable by a processing circuit to update a navigation system of a medical vehicle. The instructions include instructions for generating sensor data with a sensor, wherein the sensor data is based on a position of the occupant, instructions for determining a contour of the medical vehicle, instructions for detecting a protruding extremity of an occupant of the medical vehicle, and instructions for notifying the navigation system of the medical vehicle of the protruding extremity. Detecting the protruding extremity is based on the sensor data and the contour.

Another embodiment relates to a system for warning of a protruding object of a medical vehicle including a sensor configured to generate sensor data based on a position of the object, a feedback device, a processing circuit. The processing circuit is configured to determine a contour of the medical vehicle, detect a protruding object based on the sensor data and the contour, and generate a warning using the feedback device, wherein the warning is based on the detected protruding object.

Another embodiment relates to a system for notifying a navigation system of a medical vehicle of a protruding object including a sensor configured to generate sensor data based on a position of the object and a processing circuit. The processing circuit is configured to determine a contour of the medical vehicle, detect a protruding object of the medical vehicle, wherein detecting the protruding object is based on the sensor data and the contour, and notify the navigation system of the medical vehicle of the protruding object.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
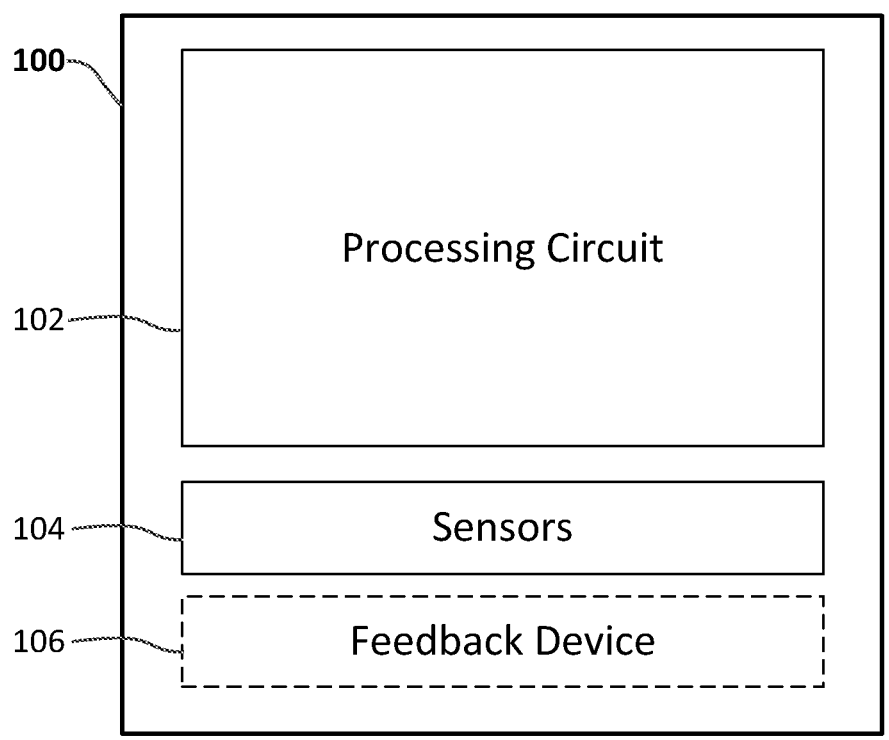
FIG. 1 is a block diagram of a system for warning of the protruding body parts of a medical vehicle occupant according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring generally to the figures, various embodiments for warning of the protruding body parts of a medical vehicle occupant are shown and described. As an occupant moves about on a medical vehicle (e.g., a wheelchair, a gurney, a mobile bed, etc.), the occupant's extremities may shift and extend beyond the normal envelope/dimensions, or contour, of the medical vehicle. For example, the occupant's leg may shift to extend off of the side of the wheelchair instead of remaining within the leg rest areas. As the medical vehicle moves, the protruding leg is prone to collisions with walls, doorways, objects, people, etc. A nurse, occupant, or other individual who is moving the medical vehicle may not immediately recognize the protruding extremity, which could lead to a collision. The contour of the medical vehicle may include general or specific dimensions of the medical vehicle, and may include the dimensions of respiratory equipment, tanks, and other aids, accessories, etc., coupled to the medical vehicle. Sensing devices and a processing circuit may be utilized to detect, and warn the nurse, occupant, or individual of the dangerous condition. Although generally referred to as extremity herein, the extremity may include an arm, a leg, a head, a foot, a hand, or any part of the body. The extremity may include clothing/protective gear that the occupant may be wearing on the extremity. The protruding extremity may be detected through the use of imaging sensors (e.g., cameras, wide-field-of-view cameras, RFID sensors, infrared devices, optical links, etc.), which are able to sense the position of an occupant and the occupant's extremities. The position of the occupant may include a position relative to the medical vehicle and may include the occupant's geospatial location. Additionally, extremity protrusions may be estimated or inferred by the processing circuit based on knowledge of the occupant's position and skeletal anatomy. For example, a non-protruding portion of the occupant may be detected (e.g., by pressure or touch sensors, etc.), and then a protruding portion may be estimated or inferred by comparing the non-protruding portion to the skeletal anatomy. Sensors such as imagers, pressure sensors, capacitance sensors, and the like, may also be used to ascertain the occupant's position and body part locations within the medical vehicle. A warning of the condition may be provided through a feedback device such as a display screen, a speaker, a mechanical feedback device, etc., or any combination of feedback devices. By providing the warning through a feedback device, the nurse, individual, or occupant may take corrective action and reposition the protruding extremity before a collision occurs.

In another scenario, as the occupant moves about on a medical vehicle, various objects or equipment (e.g., an oxygen tank, respiratory equipment, medical equipment, an I.V. drip bag stand, a flag, a cane, a walking aid, etc.) may shift and extend beyond the normal envelope/dimensions, or contour, of the medical vehicle. For example, the occupant's cane may shift to extend off of the side of the wheelchair instead of remaining within the ordinary bounds of the wheelchair. As the medical vehicle moves, the protruding cane is prone to collisions with walls, doorways, objects, people, etc. A nurse, occupant, or other individual who is moving the medical vehicle may not immediately recognize the protruding cane, which could lead to a collision. Sensing devices and a processing circuit may be utilized to detect the protruding object, and warn the nurse, occupant, or individual of the dangerous condition. The protruding object may be detected through the use of imaging sensors (e.g., cameras, wide-field-of-view cameras, RFID sensors, infrared devices, optical links, etc.), which are able to sense the position of an object relative to the medical vehicle. Additionally, object protrusions may be estimated or inferred by the processing circuit based on knowledge of the type object or an object model (e.g., including dimensions, shapes, etc.). For example, a non-protruding portion of the object may be detected and then a protruding portion may be estimated or inferred by comparing the non-protruding portion to the model of the object. Sensors such as imagers, pressure sensors, capacitance sensors, and the like, may also be used to ascertain the object's position and location with respect to the medical vehicle. A warning of the condition may be provided through a feedback device such as a display screen, a speaker, a mechanical feedback device, etc., or any combination of feedback devices. By providing the warning through a feedback device, the nurse, individual, or occupant may take corrective action and reposition the protruding object before a collision occurs.

Various embodiments for notifying a navigation system of a medical vehicle of protruding body parts are also shown and described. A patient may be moving in a motorized medical vehicle that has a navigation system (e.g., collision detection systems, automatic guidance systems, etc.). In general, such a navigation system may utilize a collision avoidance algorithm that considers the medical vehicle's contour (e.g., the vehicle's dimensions) as the system is controlling the vehicle. Sensing devices and a processing circuit may be utilized to detect a protruding extremity or object as discussed above. The processing circuit may also determine a specific or estimated amount that an extremity is protruding. The processing circuit may calculate the amount based on sensor measurement data, or the processing circuit may estimate or otherwise infer the amount based on skeletal anatomy or non-protruding body parts. The processing circuit may also determine a specific or estimated amount that an object is protruding based on sensor measurement data, or the processing circuit may estimate or otherwise infer the object protrusion amount based on a model or non-protruding portions of the object. After a protruding extremity or object is detected, the processing circuit may inform the navigation system of the condition, and the navigation system may use the provided data in its collision avoidance/detection and navigation algorithms. In some embodiments, the processing circuit calculates an updated contour of the medical vehicle, which includes the additional space or extended contour taken up by the protruding extremity or object, or both. The updated contour may generally correspond to overall medical vehicle dimensions, or may be localized to the area of the protrusion. For example, a wheelchair may be treated as if it is six inches wider if an occupant's foot is extending outside the ordinary bounds of the wheelchair by a few inches. As another example, a wheelchair may be treated as if it is twelve inches wider if an occupant's mobile oxygen tank is extending outside the ordinary bounds of the wheelchair by ten inches. The updated contour data may then be provided to the medical vehicle's navigation system.

The described systems herein may be enabled or disabled by a user as the user desires. Additionally, a user may specify preferences in order to set characteristics of warnings and sensitivity of sensors. User preferences and settings may be stored in a preference file. Default operating values may also be provided.

Referring to FIG. 1, a block diagram of system 100 for warning of a protruding extremity of a medical vehicle occupant is shown. System 100 may also be used for warning of a protruding object of a medical vehicle. System 100 may also be used for notifying a medical vehicle's navigation system of the protruding extremity or object. According to one embodiment, system 100 includes processing circuit 102, and sensors 104 for sensing information related to the occupant's position and providing the information to processing circuit 102. In some embodiments, system 100 includes feedback device 106 for providing a warning related to a protruding extremity. In other embodiments, system 100 may lack feedback device 106 and may be configured to notify the navigation system of a medical vehicle of a protruding extremity condition. In other embodiments, system 100 may provide warnings through feedback device 106 and inform the navigation system. Sensors 104 include all sensing components necessary for sensing a protruding extremity. Sensors 104 may include a single sensor device, or multiple sensors. Sensors 104 may be imaging sensors, cameras, laser sensors, radar sensors, RFID sensors, infrared sensors, optical sensors, pressure sensors, capacitive sensors, GPS sensors, etc., or any combination of sensors. Cameras or other imaging sensors may be located on the medical vehicle, or may be external to it, reporting wirelessly to the processing circuit 102. Sensors 104 are communicably coupled to processing circuit 102. Processing circuit 102 analyzes the sensor data and detects a protruding extremity based on the sensor data. Processing circuit 102 may also determine characteristics of the protruding extremity (e.g., what specific body part is protruding, an amount of protrusion, a location of protrusion, etc.). In one embodiment, processing circuit 102 generates a warning and outputs the warning to feedback device 106. Feedback device 106 may be a display screen, a speaker, a mechanical feedback device, or any device capable of providing feedback related to a protruding extremity. For example, feedback device 106 may include an LCD display screen coupled to the medical vehicle. As another example, feedback device 106 may be an external feedback device wirelessly connected to processing circuit 102 (e.g., a terminal at a nurse's station, etc.). In another embodiment, processing circuit 102 notifies a navigation system of the medical vehicle of the protruding extremity (or extremities). The navigation system may utilize the information during navigation or collision detection. Processing circuit 102 may also calculate an updated vehicle contour, including the bounds of the protruding extremity, and provide the updated contour to the navigation system.

According to one embodiment, system 100 includes processing circuit 102, and sensors 104 for sensing information related to an object's position and providing the information to processing circuit 102. In some embodiments, system 100 includes feedback device 106 for providing a warning related to a protruding object. In other embodiments, system 100 may lack feedback device 106 and may be configured to notify the navigation system of a medical vehicle of a protruding object condition. In other embodiments, system 100 may provide warnings through feedback device 106 and inform the navigation system. Sensors 104 may be generally configured as discussed above, and sensors 104 may be configured to detect both a protruding extremity and a protruding object. Accordingly, system 100 may be configured to detect a protruding extremity, object, or both. Such detection of extremities and objects may occur separately, or at the same time, and may be enabled or disabled as a user desires. Processing circuit 102 may also determine characteristics of the protruding object (e.g., what type of object is protruding, an amount of protrusion, a location of protrusion, etc.). In one embodiment, processing circuit 102 generates a warning and outputs the warning to feedback device 106. Feedback device 106 may be a feedback device as described above, and may be capable of providing feedback related to a protruding object. In another embodiment, processing circuit 102 notifies a navigation system of the medical vehicle of the protruding object (or objects). The navigation system may utilize the information during navigation or collision detection. Processing circuit 102 may also calculate an updated vehicle contour, including the bounds of the protruding object, and provide the updated contour to the navigation system. An updated contour may also include space taken up by both a protruding extremity and a protruding object.

In one embodiment, system 100 is integrated into a manual wheelchair. Processing circuit 102 is a computing device coupled to the wheelchair. Sensors 104 include a wide-field-of-view camera. Feedback device 106 includes a speaker. Processing circuit 102 accepts input from the camera and analyzes the images from the camera to determine when an occupant extends past the boundaries of the wheelchair. When a protruding extremity is detected, processing circuit 102 generates an audible alert using the speaker. In another embodiment, sensors 104 include a GPS sensor configured to provide a geospatial location. Processing circuit 102 accepts input from the camera and analyzes the images from the camera to determine when an occupant extends past the boundaries of the wheelchair, however, the protruding extremity detection is further based on the geospatial location. For example, in a location that is more open (e.g., on a sidewalk, outside, etc.), an extremity may not be considered protruding, and an alert may be suppressed. In a location that is indoors or constricted (e.g., within a hospital, etc.) the protrusion may be detected and the alert may be generated as described herein.

In one embodiment, system 100 is integrated into a manual wheelchair. Processing circuit 102 is a computing device coupled to the wheelchair. Sensors 104 include optical sensors. Feedback device 106 includes a display screen. As an example, the optical system may include a transmitter that sends a light beam to a receiver across the width of the wheelchair (e.g. along the perimeter of the wheelchair near the occupant's feet, etc.). Upon obstruction of the optical beam by the occupant, processing circuit 102 may determine that the occupant is not properly seated, and therefore has a protruding extremity. Processing circuit 102 generates a flashing warning on the display screen to alert someone of the obstruction.

In one embodiment, system 100 is integrated into a gurney. Processing circuit 102 is a computing device coupled to the gurney. Sensors 104 include an RFID (radio-frequency identification) sensor. RFID tags are coupled to the occupant of the gurney at various locations (e.g., left arm, right arm, left ankle, right ankle, etc.). Feedback device 106 includes a light and a speaker. Processing circuit 102 receives input from the RFID sensor corresponding to the RFID tags. The RFID sensor may provide distance information to processing circuit 102, or alternatively, processing circuit 102 may calculate a distance of the RFID tag. A distance may be based on a reflected signal strength from the RFID sensor to a particular RFID tag. A distance may also be based on the time it takes for a signal generated by the RFID sensor to reflect from an RFID tag and return to the RFID sensor. In some embodiments, multiple RFID sensors may each measure distances to an RFID tag, and based on the set of multiple distances, processing circuit 102 may determine a 3-D location of the RFID tag. Based on the distance information, processing circuit 102 may determine when an extremity corresponding to a particular RFID tag is protruding. Alternatively, processing circuit 102 may determine a protrusion if the RFID sensor data indicates that the RFID tag has crossed a threshold, regardless of distance information. When a protruding extremity is detected, processing circuit 102 causes the light to flash and an audible warning (e.g., a beeping noise, a siren, a pre-recorded alert, etc.) to play on the speaker.

In one embodiment, system 100 is integrated into a mobile hospital bed. Processing circuit 102 is a computing device coupled to the hospital bed. Sensors 104 include pressure sensors and capacitive sensors integrated throughout the hospital bed. Feedback device 106 includes a speaker. Processing circuit 102 receives input from the sensors. Based on the pressure data and the capacitive data, processing circuit 102 determines an occupant's position on the bed. For example, different parts of the body produce different characteristics with respect to the pressure induced on the medical vehicle's surface. By comparing various pressure points and capacitive readings, the position of an occupant's legs, arms, back, etc. may be determined. Processing circuit 102 may also compare the determined position information to skeletal models and estimate that an occupant's extremity is outside the normal contours of the bed. For example, if the pressure and capacitive data indicates that an occupant's arm is resting near the edge of the bed, and is directed off the bed, processing circuit 102 may infer that the occupant's hand is protruding from the bed. When a protruding extremity is detected, processing circuit 102 causes an audible warning to play on the speaker.

In one embodiment, system 100 is integrated into a mobile hospital bed. Processing circuit 102 is a computing device coupled to the hospital bed. Sensors 104 include cameras integrated throughout the hospital bed. Feedback device 106 includes a display screen. Processing circuit 102 receives input from the sensors. Based on the camera data, processing circuit 102 determines the position of an occupant's oxygen tank (located on a cart) on the side of the bed, and an amount the tank is protruding. Processing circuit 102 may also compare the determined position to models of oxygen tanks and estimate that the tank is outside the normal contours of the bed by a certain amount. For example, processing circuit 102 may infer that the tank is protruding a certain amount by analyzing a tank model that includes dimensional information related to a certain type of oxygen tank or a general oxygen tank. When the protruding tank is detected, processing circuit 102 generates a warning on the display screen to notify the occupant or caretaker of the oxygen tank. The scope of the present disclosure is not limited to oxygen tanks, and other objects may be detected as described herein.

In one embodiment, system 100 is integrated into an electric wheelchair. The electric wheelchair has a navigation system including collision avoidance features. Processing circuit 102 is a computing device coupled to the wheelchair. Sensors 104 include multiple wide-field-of-view cameras. Processing circuit 102 accepts input from the cameras and analyzes the images from the cameras to determine when an occupant extends past the boundaries of the electric wheelchair. When a protruding extremity is detected, processing circuit 102 calculates an updated contour of the electric wheelchair to account for the protruding extremity. The updated contour may include an extended contour corresponding to overall medical vehicle dimensions, or may be localized to the area of the protruding extremity. Processing circuit 102 transmits this updated contour information to the navigation system. Processing circuit 102 may format the data related of the updated contour and may communicate with the navigation system according to a protocol defined by system 100 or defined by the navigation system.

In one embodiment, system 100 is integrated into a gurney. Processing circuit 102 is a computing device coupled to the gurney. Sensors 104 include an RFID (radio-frequency identification) sensor. RFID tags are coupled to medical equipment at various locations (e.g., on an oxygen tank, an I.V. stand, etc.). Feedback device 106 includes a light and a speaker. Processing circuit 102 receives input from the RFID sensor corresponding to the RFID tags. The RFID sensor may be configured to provide distance information to processing circuit 102 as discussed above, or alternatively, processing circuit 102 may calculate a distance of the RFID tag. Based on the distance information, processing circuit 102 may determine when an object corresponding to a particular RFID tag is protruding outside the contour of the medical vehicle. Alternatively, processing circuit 102 may determine a protrusion if the RFID sensor data indicates that the RFID tag has crossed a threshold, regardless of distance information. When a protruding object is detected, processing circuit 102 causes the light to flash and an audible warning (e.g., a beeping noise, a siren, a pre-recorded alert, etc.) to play on the speaker.

In one embodiment, system 100 is integrated into a manual wheelchair. Processing circuit 102 is a computing device coupled to the wheelchair. Sensors 104 include a wide-field-of-view camera. Feedback device 106 includes a speaker. Processing circuit 102 accepts input from the camera and analyzes the images from the camera to determine when an object extends past the boundaries of the wheelchair. When a protruding object is detected, processing circuit 102 generates an audible alert using the speaker.

In one embodiment, system 100 is integrated into an electric wheelchair. The electric wheelchair has a navigation system including collision avoidance features. Processing circuit 102 is a computing device coupled to the wheelchair. Sensors 104 include multiple cameras. Processing circuit 102 accepts input from the cameras and analyzes the images from the cameras to determine when an object extends past the boundaries of the electric wheelchair. When a protruding object is detected, processing circuit 102 calculates an updated contour of the electric wheelchair to account for the protruding object. The updated contour may include an extended contour corresponding to overall medical vehicle dimensions, or may be localized to the area of the protruding object. Processing circuit 102 transmits this updated contour information to the navigation system. Processing circuit 102 may format the data related of the updated contour and may communicate with the navigation system according to a protocol defined by system 100 or defined by the navigation system.

Figure 2:
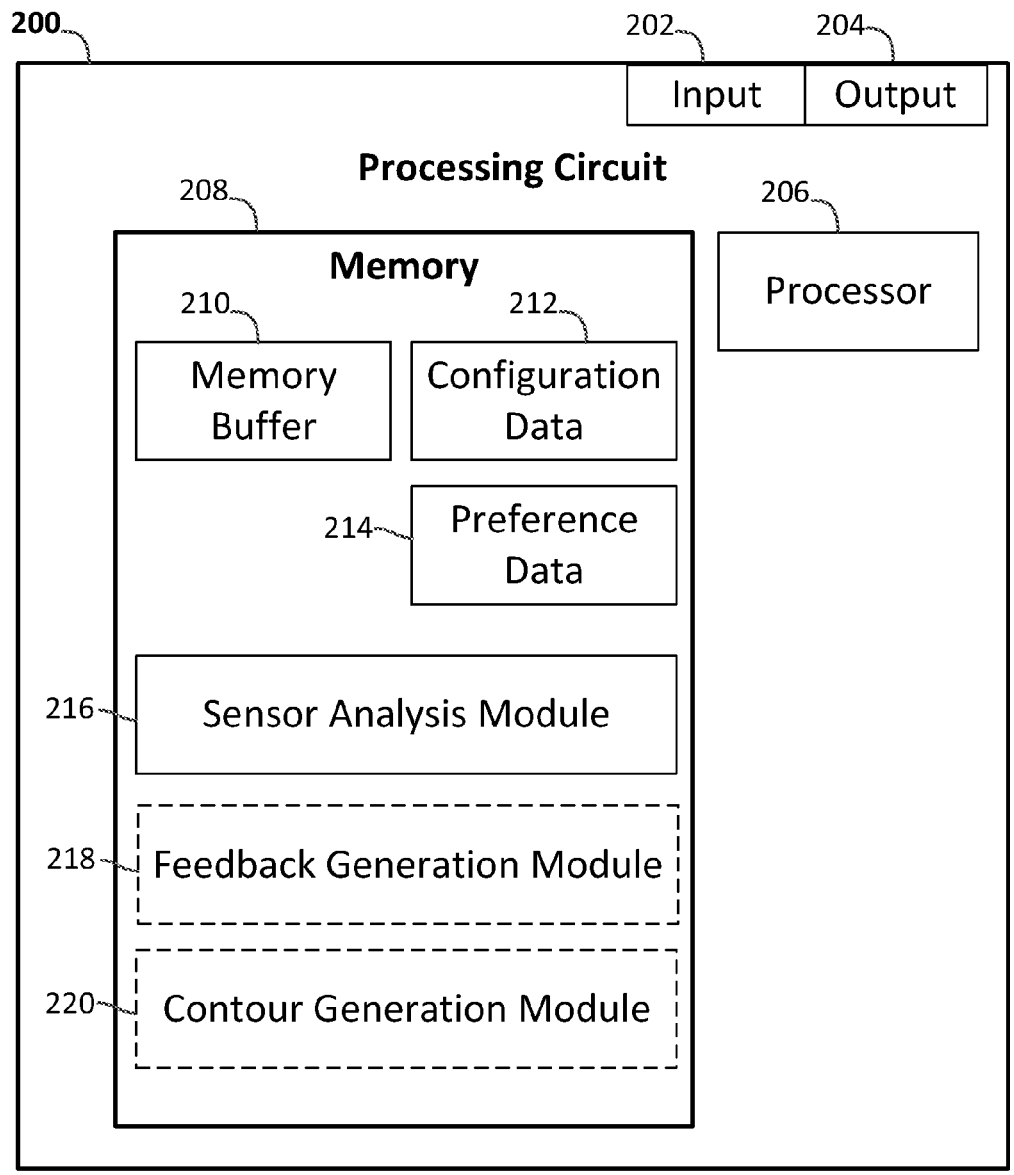
FIG. 2 is a block diagram of a processing circuit according to one embodiment.

Referring to FIG. 2, a detailed block diagram of processing circuit 200 for completing the systems and methods of the present disclosure is shown according to one embodiment. Processing circuit 200 may be processing circuit 102 of FIG. 1. Processing circuit 200 is generally configured to accept input from at least one sensor. Processing circuit 200 is further configured to receive configuration and preference data. Input data may be accepted continuously or periodically. Processing circuit 200 uses the input data to detect when an occupant's body part extends past the ordinary contour of a medical vehicle. The ordinary contour is generally based on the dimensions of the particular medical vehicle. Processing circuit 200 may automatically detect the ordinary contour of a medical vehicle, or may receive contour information. For example, a model of the medical vehicle may be provided by configuration data 212. Processing circuit 200 analyzes data provided by the sensor(s) to determine when the occupant moves outside of the contour, and is therefore vulnerable to a collision. Based on any detected protrusions, procession circuit 200 may generate and output a warning using a feedback device, or processing circuit 200 may notify a navigation system. Processing circuit 200 may also generate updated contour maps that take into account the space occupied by any protrusions. In determining protrusions and generating contours, processing circuit 200 may make use of machine learning, artificial intelligence, interactions with databases and database table lookups, pattern recognition and logging, intelligent control, neural networks, fuzzy logic, etc.

According to one embodiment, processing circuit 200 includes processor 206. Processor 206 may be implemented as a general-purpose processor, an application specific integrated circuit (ASIC), one or more field programmable gate arrays (FPGAs), a digital-signal-processor (DSP), a group of processing components, or other suitable electronic processing components. Processing circuit 200 also includes memory 208. Memory 208 is one or more devices (e.g., RAM, ROM, Flash Memory, hard disk storage, etc.) for storing data and/or computer code for facilitating the various processes described herein. Memory 208 may be or include non-transient volatile memory or non-volatile memory. Memory 208 may include database components, object code components, script components, or any other type of information structure for supporting the various activities and information structures described herein. Memory 208 may be communicably connected to processor 206 and include computer code or instructions for executing the processes described herein.

Memory 208 includes memory buffer 210. Memory buffer 210 is configured to receive a data stream from a sensor (e.g. sensors 104, etc.) through input 202. For example, the data may include a real-time stream of sensor data, etc. The data received through input 202 may be stored in memory buffer 210 until memory buffer 210 is accessed for data by the various modules of memory 208. For example, sensor analysis module 216, feedback generation module 218, and contour generation module 220 each can access the data that is stored in memory buffer 210.

Memory 208 further includes configuration data 212. Configuration data 212 includes data related to processing circuit 200. For example, configuration data 212 may include information related to interfacing with other components (e.g., sensors of system 100 of FIG. 1, a navigation system of a medical vehicle, etc.). This may include the command set needed to interface with a computer system used transfer user settings or otherwise set up the system. This may further include the command set need to generate graphical user interface (GUI) controls, menus, and visual information. As another example, configuration data 212 may include the command set needed to interface with communication components (e.g., a universal serial bus (USB) interface, a Wi-Fi interface, an Ethernet interface, etc.). In this manner, processing circuit 200 may format data for output via output 204 to allow a user to configure the systems as described herein. Processing circuit may also format visual information to generate visual warnings for display on a display device. Processing circuit 200 may also format audio data for output via output 204 to allow a speaker to create sound. Processing circuit may also generate commands necessary to drive a mechanical feedback device (e.g. a device that creates a vibration). Such a vibration may be selected to be detectable by the medical vehicle's occupant (e.g., on armrests or a seat). Such a vibration may be selected to be detectable by a person pushing the medical vehicle, (e.g., via a wheelchair's handles). Configuration data 212 may include information as to how often input should be accepted from a sensor. As another example, configuration data 212 may include default values required to initiate the device and initiate communication with sensors or peripheral systems. Configuration data 212 further includes data to configure communication between the various components of processing circuit 200.

Processing circuit 200 further includes input 202 and output 204. Input 202 is configured to receive a data stream (e.g., a digital or analog stream of data from sensors), configuration information, and preference information. Output 204 is configured to provide an output to a feedback device, a medical vehicle navigation system, or components of the systems as described herein.

Memory 208 further includes modules 216, 218, and 220 for executing the systems and methods described herein. Modules 216, 218, and 220 are configured to receive sensor data, configuration information, user preference data, and other data as provided by processing circuit 200. Modules 216, 218, and 220 are generally configured to analyze sensor data, detect a protruding body part from an occupant of a medical vehicle, provide feedback related to detected protrusions, inform medical vehicle navigation systems of protrusions, and generate updated medical vehicle contours that account for the protrusions. Modules 216, 218, and 220 may be further configured to operate according to a user's preferences. In this manner, certain feedback characteristics and sensor sensitivities may be adjusted according to a user's desires.

Sensor analysis module 216 is configured to receive sensor data from various sensors (e.g., sensors 104 of FIG. 1, etc.). The sensor data may include distance related data, orientation related data, a range, or general 3-D spatial information. The sensor data may be provided through input 202 or through memory buffer 210. Sensor analysis module 216 scans the sensor data and analyzes the data to detect the position of the occupant and her extremities. Sensor analysis module 216 may further determine the particular type of extremity (e.g., arm, leg, foot, head, hand, etc.). Sensor analysis module 216 may scan and analyze the sensor data to detect various objects (e.g., a cane, medical equipment, etc.). In one embodiment, sensor analysis module 216 scans to automatically detect all objects within the sensor data. In another embodiment, sensor analysis module 216 analyzes the sensor data for certain types of objects. The types of objects may be provided by configuration data or user setting data. Additionally, various models of objects may be accessed in detecting an object. Sensor analysis module 216 compares the positioning of the occupant and extremities to the contour of the medical vehicle. Sensor analysis module 216 also compares the positioning of the objects to the contour of the medical vehicle. The contour generally corresponds to the dimensions of the area of space taken up by the medical vehicle (e.g. a maximum length and width, etc.). For example, a particular wheelchair model may have a footprint that is 3.5 ft. wide by 4 ft. long. As another example, a particular hospital gurney may have a footprint that is 4 ft wide by 6 ft long. The contour in these situations may correspond to the perimeter around the space taken up by the footprint. The contour may be precisely specified to correspond to all changes in dimensions of the medical vehicle, or may be a more general square/rectangle shape corresponding to the maximum dimensions occupied by the medical vehicle. As another example, a particular wheelchair model may have a footprint that is 3 ft wide by 4 ft long, but may have armrests such that the width of the wheelchair is 3.5 ft at the armrest level. The contour in this scenario may correspond to the length of the wheelchair, and the width of the armrests, as opposed to the width at the footprint of the wheelchair. The contour of a medical vehicle may either be provided by pre-stored medical vehicle profiles or contours (e.g., stored in configuration data, etc.), may be based on wheelchair model data, or may be detected by sensor analysis module 216. Sensor analysis module 216 may utilize typical boundary detection algorithms in determining the contour of a medical vehicle.

Sensor analysis module 216 may determine that an occupant's extremity or object is outside of the medical vehicle contour through a variety of methods. A particular method may correspond to the type of sensors in use. Any of the methods of detection discussed herein may be combined or used individually. For example, in one embodiment utilizing a wide-field-of-view camera, sensor analysis module 216 receives image data. Sensor analysis module 216 analyzes the image data to detect the occupant's position using body detection algorithms. As the body of the occupant is detected, sensor analysis module 216 compares the location of the extremities or objects to the contour of the medical vehicle. If an extremity is determined to be outside of the contour, then sensor analysis module 216 provides this information to feedback generation module 218, contour generation module 220, or both. Typically, when an extremity is outside of the contour, it is at risk of collision, for example, with a doorway, another object, etc. However, the amount that an extremity or object must be outside the contour before it is considered a risk may be adjusted (e.g., through thresholds stored in configuration data 212 or preference data 214.). In this manner, a nurse, or occupant, may customize the particular system in use such that a threshold must be reached before the system generates a collision warning or updates contour values. In one embodiment, sensor analysis module 216 receives geospatial information from a GPS sensor, and analyzes the geospatial information in determining a protruding extremity. In this manner, the location of the medical vehicle/occupant may be used in determining distance thresholds that must be reached before the system considers an extremity as protruding. Any data generated by sensor analysis module may be provided to any of the modules of processing circuit 200.

In one embodiment utilizing optical/laser link sensors, sensor analysis module 216 receives data related to objects crossing the path of the optical/laser links. For example, if the optical links are arranged around the perimeter of the medical vehicle, the sensors may provide a signal to sensor analysis module 216 when the occupant's leg crosses the optical link and protrudes outside the contour of the medical vehicle. Such optical systems may be used in conjunction with other sensors described herein. For example, after an optical link sensor is triggered, a camera sensor may be used to determine an amount of a protrusion through analysis of image data provided by the camera sensor. As another example, capacitive and pressure sensors may be used to determine the general position of an occupant in the medical vehicle. Such pressure and capacitive sensors may be mounted in the seat and the backrest areas of the medical vehicle. Sensor analysis module 216 may analyze the position data and compare it to models of the human body (e.g., skeletal models, etc.) and estimate an amount that an extremity is protruding based on knowledge of body interconnectivity (e.g., the hand is connected to the forearm, etc.). The models of the human body may be general models according to average human proportions, or may be tailored to the dimensions of a particular occupant. Such models may be stored in configuration data 212 or preference data 214. In some embodiments, sensor analysis module 216 may be configured to infer protrusions based on pressure or capacitive data alone.

In one embodiment utilizing sensors coupled to the occupant, sensor analysis module 216 may monitor sensor data for indications that an extremity has moved beyond the safe contours of the medical vehicle. For example, an RFID sensor system may be mounted throughout the perimeter of the medical vehicle, and the occupant may have RFID tags coupled (e.g., with a wristband, etc.) to her wrists and ankles. If the RFID tag crosses the bounds of the RFID sensor system, the RFID system can provide appropriate data to the sensor analysis module 216, which may then determine that an extremity is protruding. The protrusion determination may be may in conjunction with knowledge of the occupant's body position as discussed above, or may be dependent solely on the RFID tag crossing the RFID sensor. Additionally, some RFID sensor systems are capable of determining a distance from an RFID tag as discussed above. Such distance information may be utilized by sensor analysis module 216 in determining the amount of a protrusion.

In one embodiment utilizing infrared sensors, sensor analysis module 216 may analyze heat map data corresponding to the heat signature of an occupant. Sensor analysis module 216 scans the heat map to determines the locations of the extremities of the occupant, and then compares the locations to the contour of the medical vehicle. If an extremity is determined to be extending beyond the contour, sensor analysis module 216 may determine that the extremity is protruding, and thus further action may be taken.

Feedback generation module 218 receives data from sensor analysis module 216 related to a protruding extremity. This data may include a type of extremity, a protrusion amount, a protrusion location, etc. Based on the received data, feedback generation module 218 generates feedback (e.g., a warning) to be output via a feedback device. Feedback devices may include display devices, network devices, audio devices, mechanical devices, etc. For example, in one embodiment, upon detecting a protruding extremity by sensor analysis module 216, feedback generation module 218 generates signals necessary to create an audio alert (e.g., a beep, a siren sound, etc.) to be output on a speaker. In another embodiment, feedback generation module 218 generates a user interface warning to be output on a display screen. Such a user interface warning may include details of the protruding extremity or object (e.g., "occupant's left leg is outside the safe bounds of the wheelchair!", etc.). As another example, feedback generation module 218 may receive geospatial information from a GPS sensor, and include the location of the medical vehicle/occupant in the warning. In another embodiment, feedback generation module 218 generates the signals necessary to cause a warning light to flash. In another embodiment, feedback generation module 218 generates signals necessary to cause a mechanical feedback device to vibrate. It should be understood that the scope of the present application is not limited to a particular type of warning or feedback device, and embodiments may include multiple types of feedback devices. By using such feedback devices, a nurse, the occupant, or other individual may notice that the occupant is in danger of collision, and may take appropriate corrective action. Any of the feedback mechanisms and warnings described herein may be customized according to feedback profiles or user preferences, which may be stored in configuration data 212 or preference data 214.

Contour generation module 220 receives data from sensor analysis module 216 related to a protruding extremity, and notifies a navigation system of a medical vehicle of the protruding extremity. Contour generation module 220 also receives data from sensor analysis module 216 related to a protruding object, and notifies a navigation system of a medical vehicle of the protruding object. For example, a motorized wheelchair may include a navigation system with anti-collision features. Such an anti-collision system may use radar, or other means, to scan a doorway and measure the width of the doorway opening. In some embodiments, the anti-collision system may obtain the width of the doorway from an externally supplied map or database or from geospatial information. A GPS sensor of the navigation system or a GPS sensor that is part of the systems described herein may provide such geospatial information. Based on the contour (e.g., the width, etc.) and orientation of the wheelchair, the navigation and anti-collision systems may safely steer the wheelchair through the doorway opening. Contour generation module 220 generates appropriate signals to communicate with such navigations systems. In this manner, contour generation module 220 may warn the navigation system that an extremity of the occupant is outside the ordinary contours of the medical vehicle, and the navigation system may take appropriate action (e.g., pausing the movement of the medical vehicle, changing the path of the medical vehicle, etc.). Contour generation module 220 may also warn the navigation system that the medical vehicle should be treated as having an updated contour due to the space taken up by a protruding object. In another embodiment, contour generation module 220 generates an updated contour that takes the protruding extremity into account, and provides the updated contour to the navigation system. In another embodiment, contour generation module 220 generates an updated contour that takes the protruding object into account, and provides the updated contour to the navigation system. Contour generation module 220 may access medical vehicle contour data stored in configuration data 212 or as generated by sensor analysis module 216, as discussed above. In this manner, the navigation system and anti-collision mechanisms of the medical vehicle may dynamically adjust the values used related to space occupied by the medical vehicle to compensate for the additional space taken by the protruding extremity and/or object. For example, after receiving updated contour data from contour generation module 220, the navigation system may treat a medical vehicle as being 4 ft. wide, as opposed to an ordinary 3.5 ft, and thus the navigation system may safely steer the medical vehicle to avoid collisions with the protruding extremity and/or object.

In one embodiment, contour generation module 220 updates a contour across an entire span of the medical vehicle. For example, if contour generation module 220 receives data from sensor analysis module 216 that indicates an occupant's leg is extended beyond the right-side boundary of the medical vehicle by 10 inches, contour generation module 220 may extend the width of the contour to the right side by 10 inches. As another example, if contour generation module 220 receives data from sensor analysis module 216 that indicates an occupant's cane is extended beyond the right-side boundary of the medical vehicle by 10 inches, contour generation module 220 may extend the width of the contour to the right side by 10 inches. Contour generation module 220 may add additional buffer space to the contour for additional safety (e.g., extending the right-side boundary by 15 inches instead of 10 inches as in the previously discussed examples).

In one embodiment, contour generation module 220 updates a contour in a localized manner. For example, if contour generation module 220 receives data from sensor analysis module 216 that indicates an occupant's foot is extended beyond the left-side boundary of the medical vehicle by 5 inches, contour generation module 220 may extend the width of the contour area around the extended foot by 5 inches, but not change the contour in other regions, such as above or behind the extended foot. As another example, if contour generation module 220 receives data from sensor analysis module 216 that indicates an occupant's I.V. drip bag stand is extended beyond the left-side boundary of the medical vehicle by 15 inches, contour generation module 220 may extend the width of the contour area around the I.V. drip bag stand by 15 inches, but not change the contour in other regions, such as above or behind the stand. Contour generation module 220 may add additional buffer space to the contour for additional safety.

Figure 3:
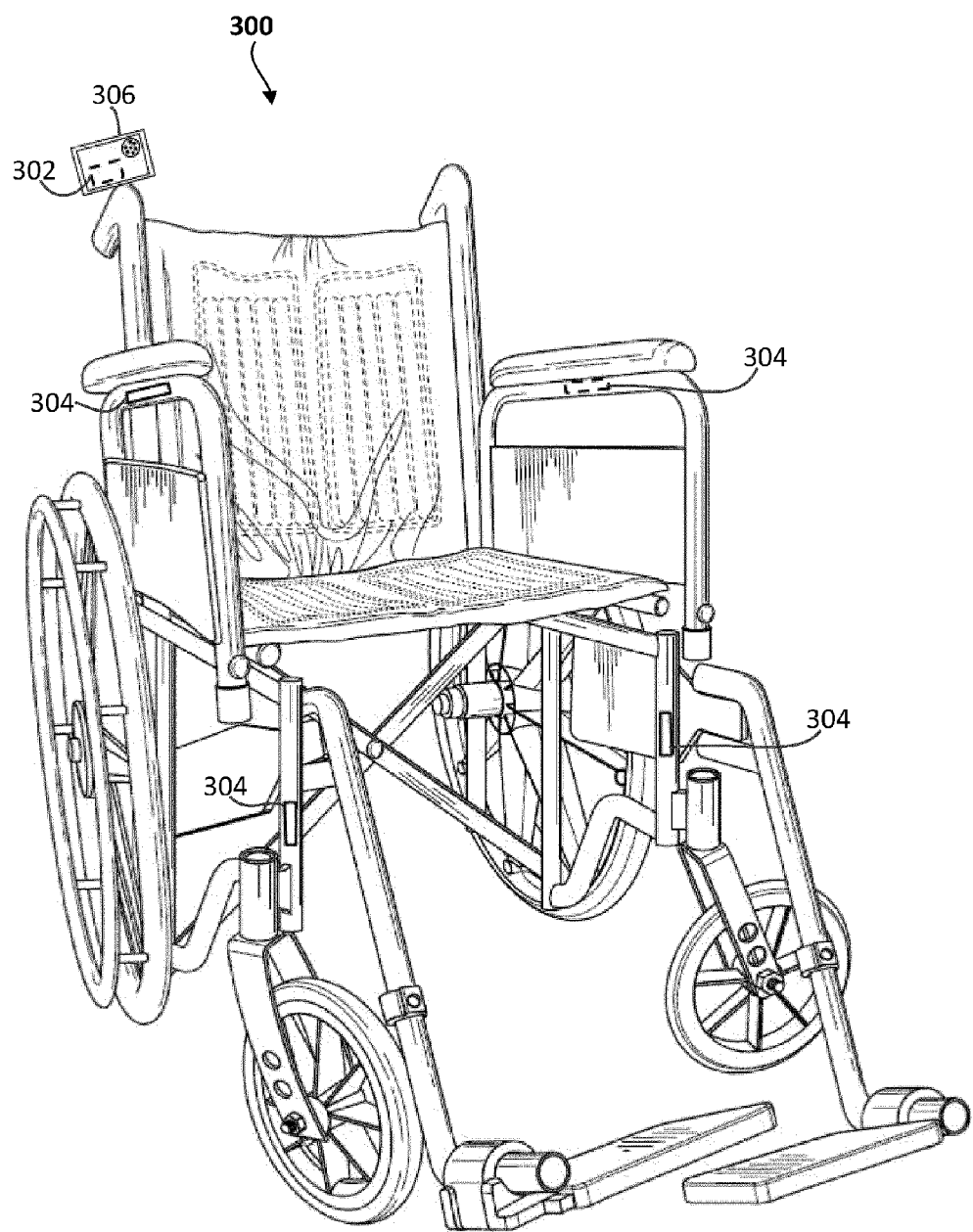
FIG. 3 is a schematic diagram of a manual wheelchair according to one embodiment.

Referring to FIG. 3, a schematic diagram of manual wheelchair 300 is shown according to one embodiment. Manual wheelchair 300 has been equipped with the systems described herein and includes processing circuit 302, sensors 304, and feedback device 306. Processing circuit 302 may be the processing circuit of feedback device 306. For example, feedback device 306 may be a tablet computer coupled to sensors 304. The tablet computer includes a screen for displaying visual warnings, and a speaker for audio warnings. Although feedback device 306 is depicted as a tablet computer, feedback device 306 may include any of the feedback means described herein. Sensors 304 may include various sensors coupled to wheelchair 300, or affixed to an occupant of wheelchair 300. In one embodiment, sensors 304 include a camera and multiple optical sensors. In another embodiment, sensors 304 include pressure sensors, capacitive sensors, and optical link sensors. In another embodiment, sensors 304 include RFID sensors and a camera. In another embodiment, sensors 304 include a radar sensor. In another embodiment, sensors 304 include an infrared sensor. The scope of the present application is not limited to a particular arrangement or selection of sensors or feedback devices.

Figure 4:
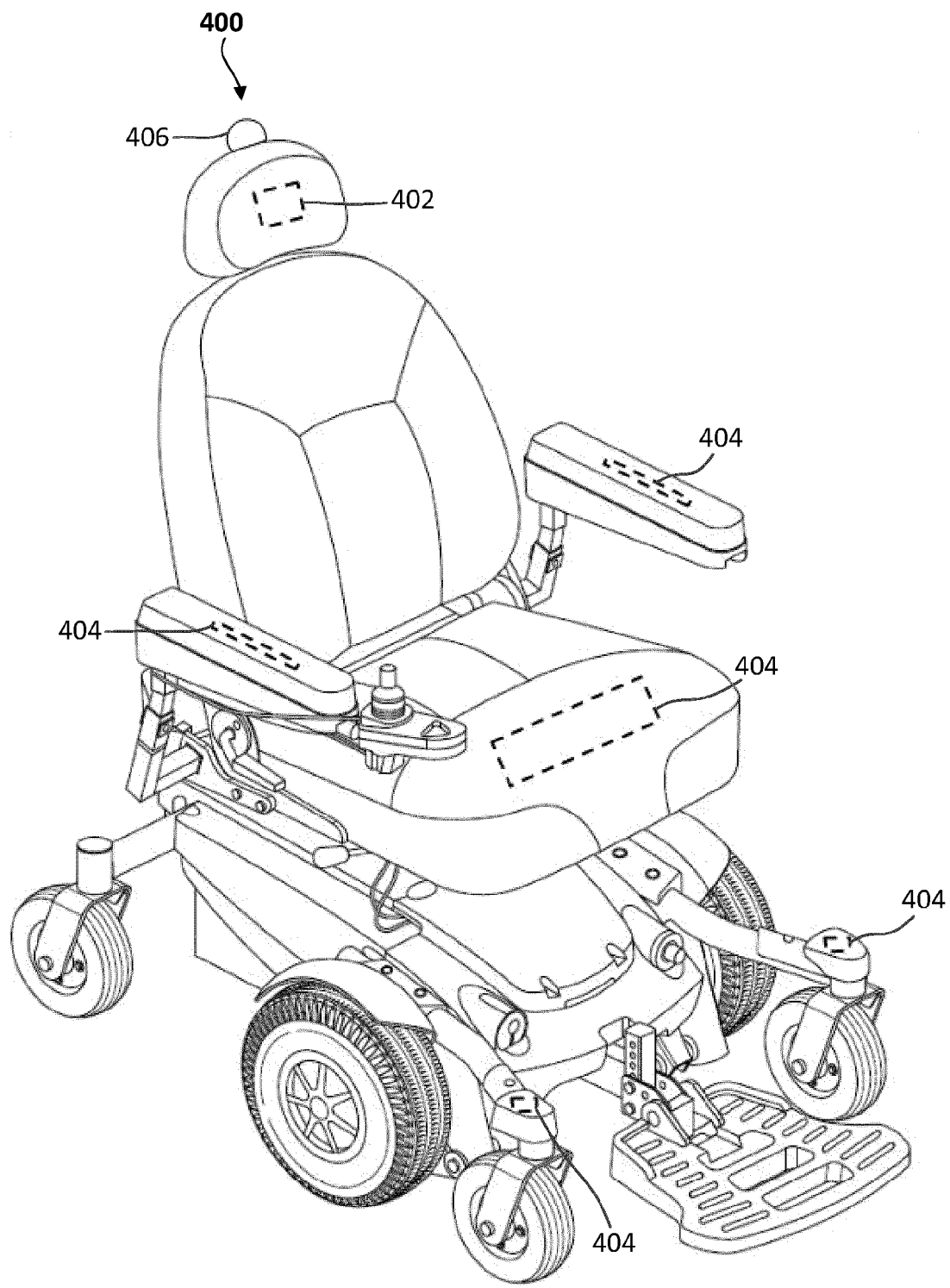
FIG. 4 is a schematic diagram of a motorized wheelchair according to one embodiment.

Referring to FIG. 4, a schematic diagram of motorized wheelchair 400 is shown according to one embodiment. Motorized wheelchair 400 has been equipped with the systems described herein and includes processing circuit 402, sensors 404, and feedback device 406. Processing circuit 402 is depicted as a system controller embedded within the headrest of motorized wheelchair 400. Processing circuit 402 may be part of the general control circuit of the motorized wheelchair. As depicted, sensors 404 may include a sensor embedded within the seat and armrests of motorized wheelchair 400. As an example, these sensors may be pressure or capacitive sensors as discussed above. Sensors 404 may also include optical link sensors affixed near the footrests of motorized wheelchair 400. Feedback device 406 is depicted as a warning light coupled to the headrest of the wheelchair, and may be used to warn a nurse when a protruding extremity is detected.

Figure 5:
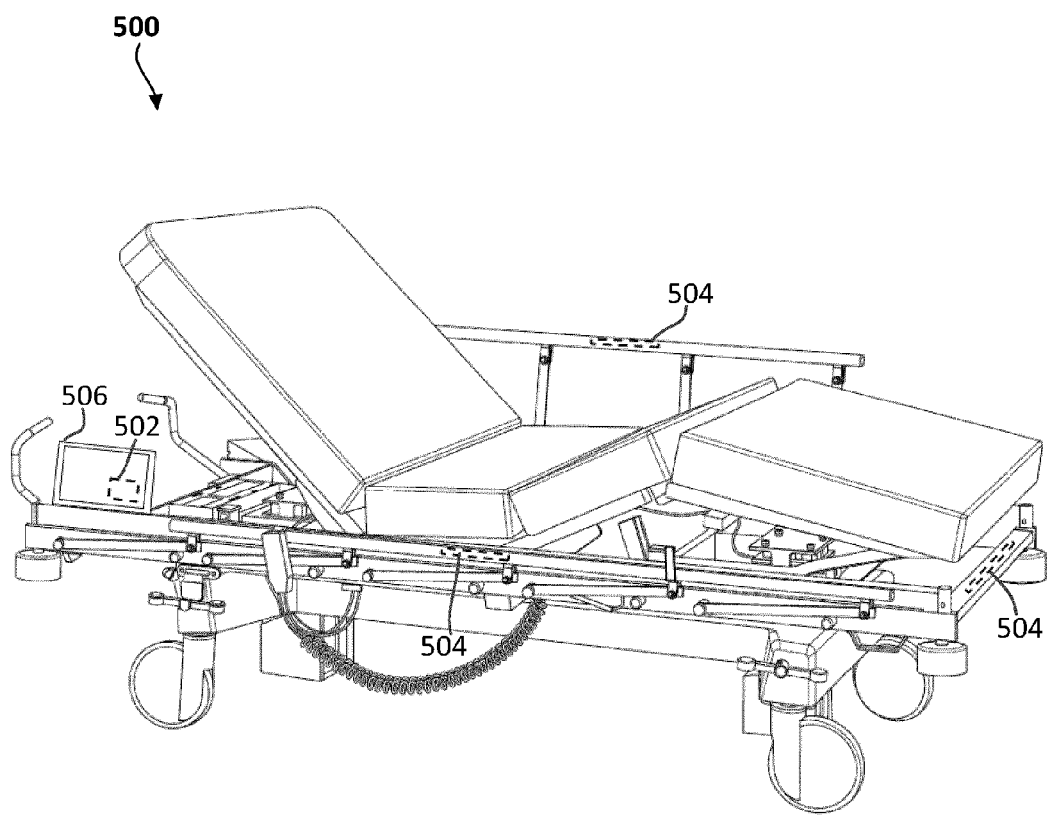
FIG. 5 is a schematic diagram of a hospital gurney according to one embodiment.

Referring to FIG. 5, a schematic diagram of hospital gurney 500 is shown according to one embodiment. Hospital gurney 500 has been equipped with the systems described herein and includes processing circuit 502, sensors 504, and feedback device 506. In one embodiment, feedback device 506 is a touch screen terminal coupled to the gurney, and processing circuit 502 is the processor of the touch screen terminal. Sensors 504 include sensors affixed throughout the perimeter of the hospital gurney. The particular sensors 504 may be any of the sensor types discussed herein.

Figure 6A:
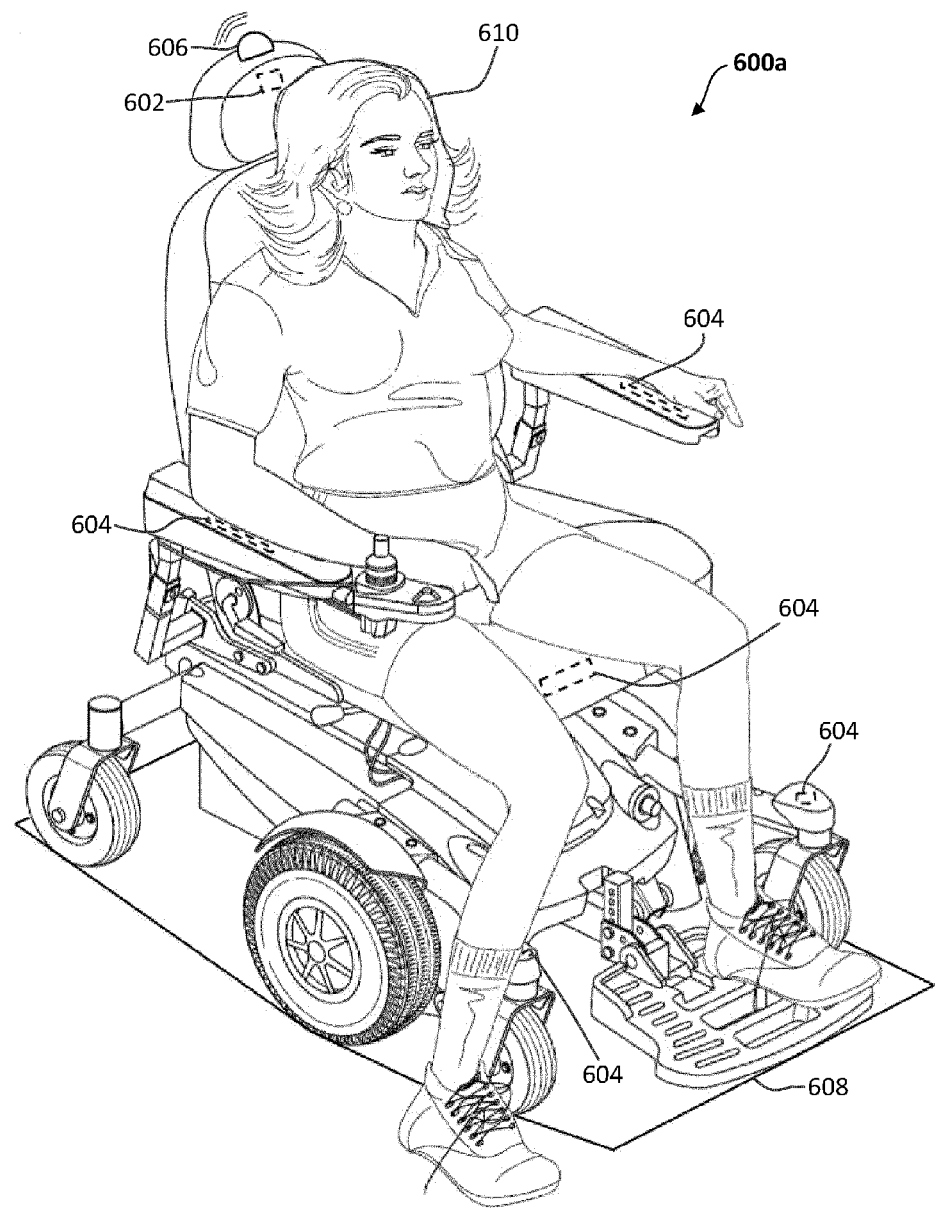
FIG. 6a is a schematic diagram of a wheelchair according to one embodiment.

Referring to FIG. 6a, a schematic of motorized wheelchair 600a is shown according to one embodiment. Motorized wheelchair 600a is configured to warn of a protruding body parts of wheelchair occupant 610. Motorized wheelchair 600a includes processing circuit 602, sensors 604, and feedback device 606. Feedback device 606 is depicted as a speaker device for generating an audible warning. Contour 608 of motorized wheelchair 600a is also depicted. Contour 608 may have been specified via configuration data or may have been automatically detected by sensors 604 as discussed above. The right foot of occupant 610 is shown as protruding beyond the right boundary of contour 608. Sensors 604 provide sensor data to processing circuit 602, which detects the right foot based on the sensor data, and compares the foot location to contour 608. Processing circuit 602 determines that the right foot is protruding and causes feedback device to generated a warning tone.

Figure 6B:
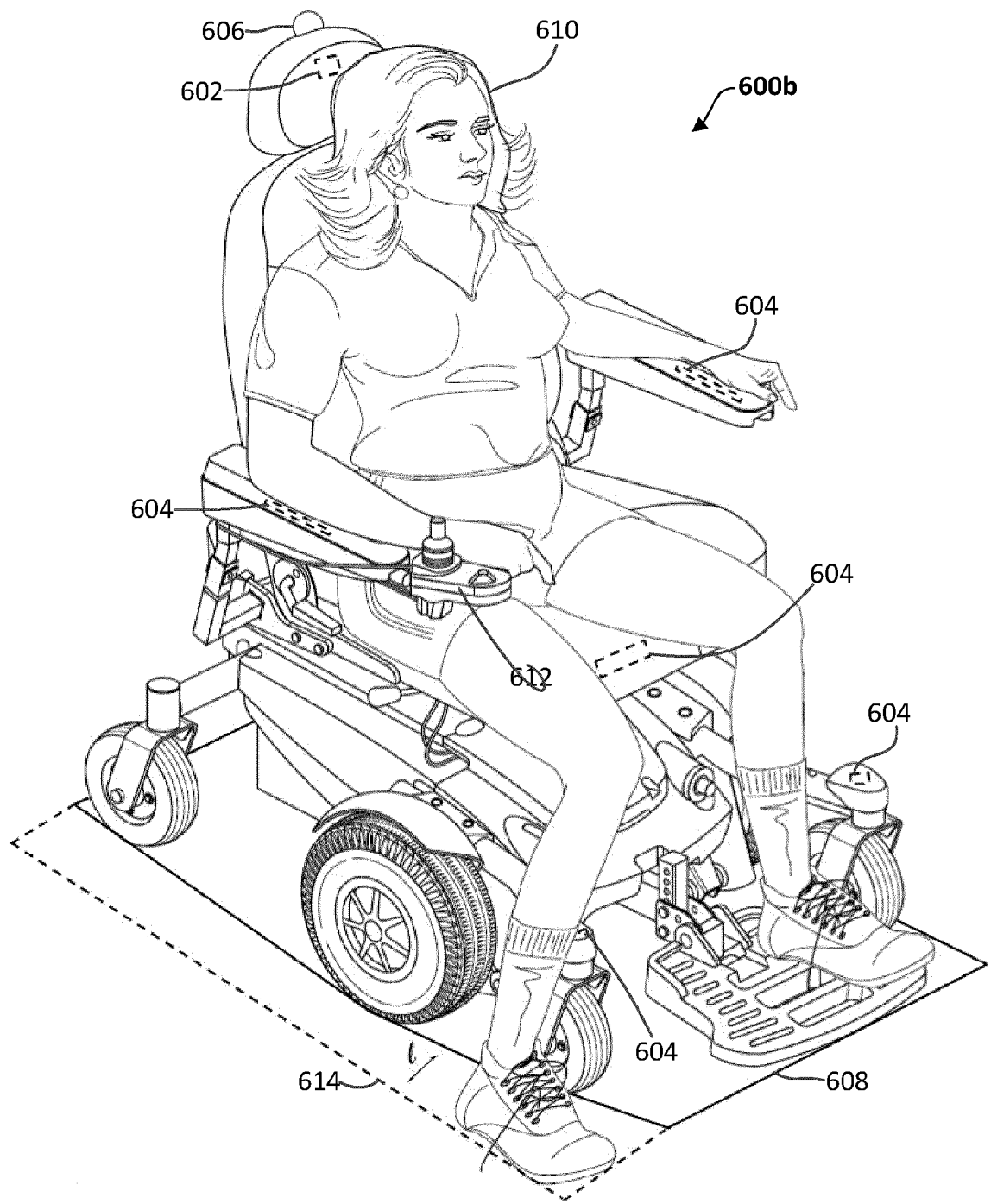
FIG. 6b is a schematic diagram of a wheelchair and an updated contour according to one embodiment.

Referring to FIG. 6b, a schematic of motorized wheelchair 600b is shown according to one embodiment. Motorized wheelchair 600b is similar to motorized wheelchair 600a of FIG. 6a, but also includes navigation system 612. Navigation system 612 has anti-collision features as discussed herein. The right foot of occupant 610 is shown as protruding beyond the right boundary of contour 608. Sensors 604 provide sensor data to processing circuit 602, which detects the protruding foot and compares it to contour 608. Processing circuit 602 calculates the amount l that the right foot is protruding and generates updated contour 614 to include the additional space occupied by the protruding foot. The width of contour 608 is depicted as being updated along the entire right span of motorized wheelchair 600b. Updated contour 614 also includes the areas of contour 608 that were unaffected by the protruding extremity. Updated contour 614 is provided to navigation system 612.

Figure 6C:
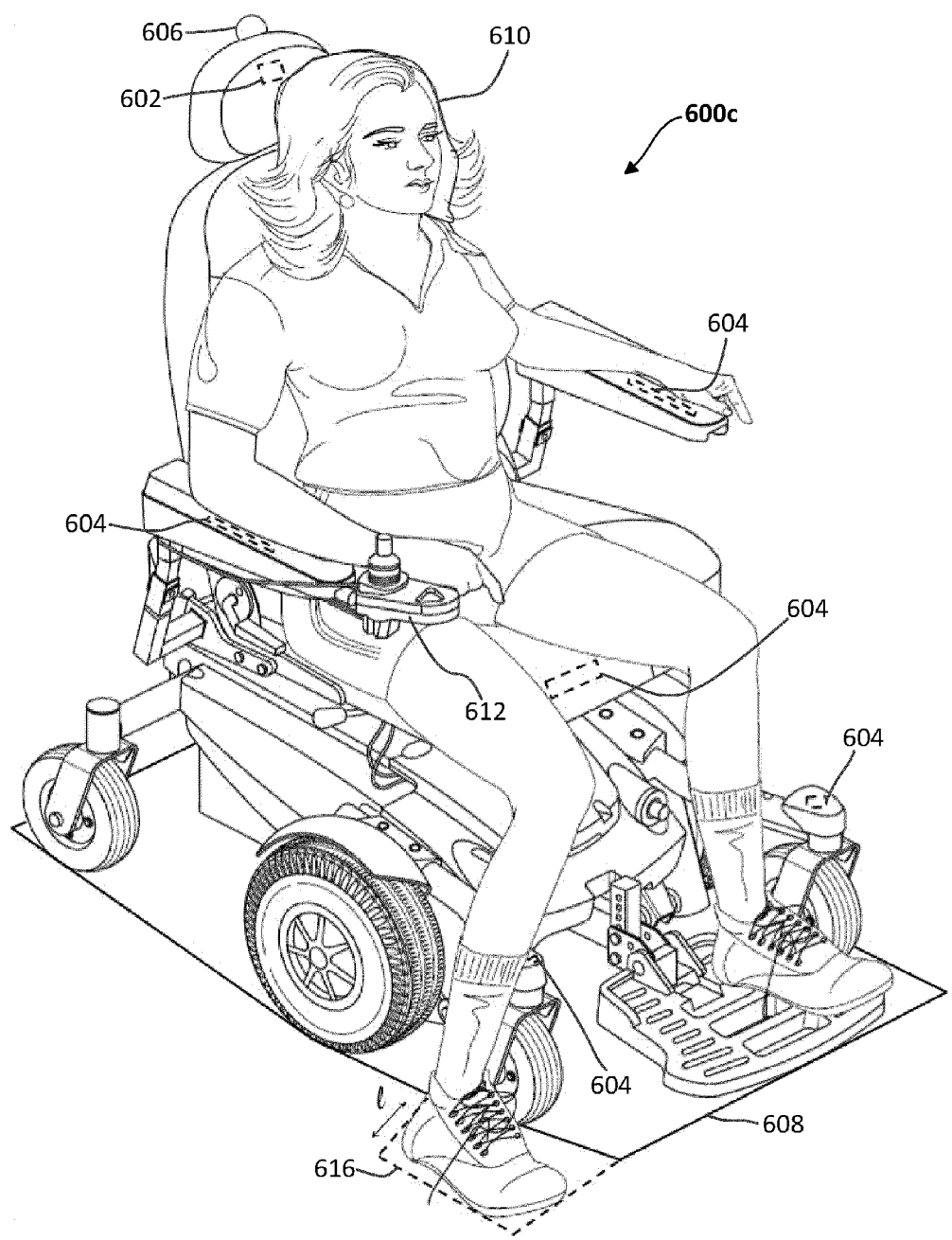
FIG. 6c is a schematic diagram of a wheelchair and an updated contour according to one embodiment.

Referring to FIG. 6c, a schematic of motorized wheelchair 600c is shown according to one embodiment. Motorized wheelchair 600c is similar to motorized wheelchair 600a of FIG. 6a, but includes navigation system 612. Navigation system 612 has anti-collision features as discussed herein. The right foot of occupant 610 is shown as protruding beyond the right boundary of contour 608. Sensors 604 provide sensor data to processing circuit 602, which detects the protruding foot and compares it to contour 608. Processing circuit 602 calculates the amount l that the right foot is protruding and generates updated contour 616 to include the additional space occupied by the protruding foot. Contour 608 is depicted as being updated locally, only around the area of the protruding foot. Updated contour 616 also includes the areas of contour 608 that were unaffected by the protruding extremity. Updated contour 616 is provided to navigation system 612.

Figure 6D:
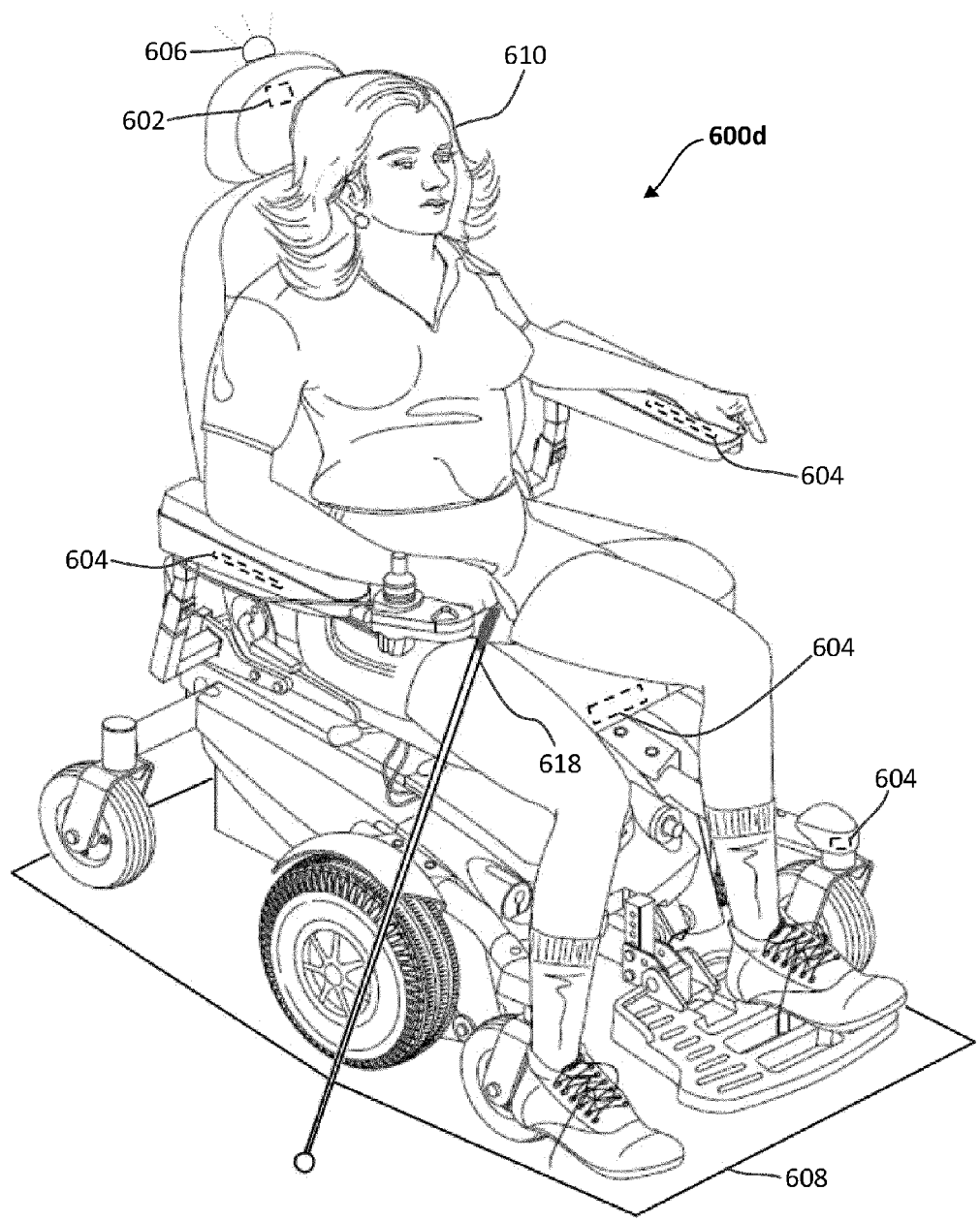
FIG. 6d is a schematic diagram of a wheelchair according to one embodiment.

Referring to FIG. 6d, a schematic of motorized wheelchair 600d is shown according to one embodiment. Motorized wheelchair 600d is configured to warn of a protruding object 618. Motorized wheelchair 600d includes processing circuit 602, sensors 604, and feedback device 606. Feedback device 606 is depicted as a speaker device for generating an audible warning. Contour 608 of motorized wheelchair 600d is also depicted. Contour 608 may have been specified via configuration data or may have been automatically detected by sensors 604 as discussed above. Occupant 610 is shown as grasping object 618 (depicted as a cane), which is protruding beyond the right boundary of contour 608. Sensors 604 provide sensor data to processing circuit 602, which detects the cane, and compares the cane's location to contour 608. Processing circuit 602 determines that the cane is protruding outside of the bounds of contour 608 and causes feedback device to generated a warning tone. Although depicted as a cane, object 618 may include other objects (e.g., an oxygen tanks, respiratory equipment, medical equipment, an I.V. drip bag stand, a flag, etc.).

Figure 6E:
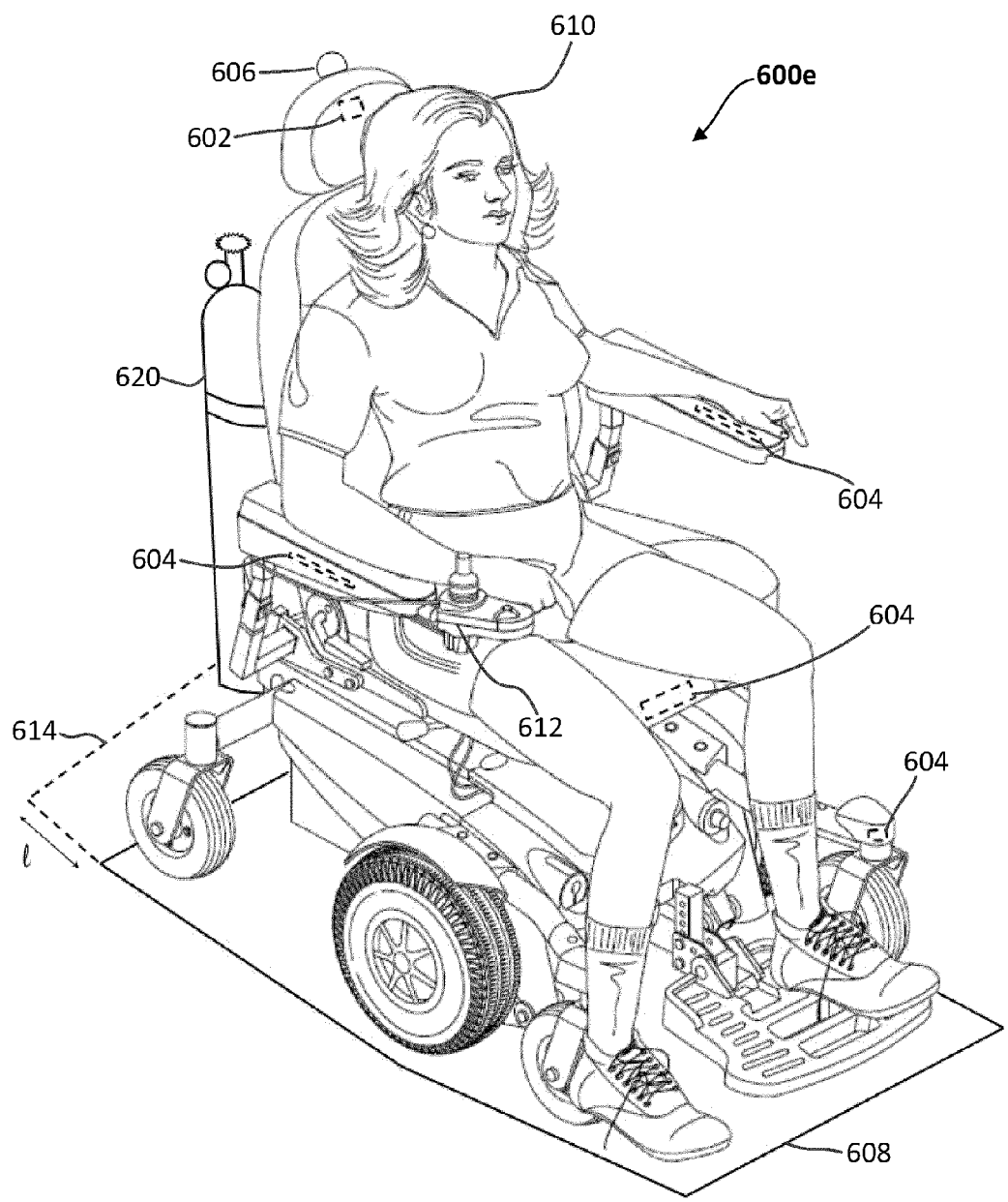
FIG. 6e is a schematic diagram of a wheelchair and an updated contour according to one embodiment.

Referring to FIG. 6e, a schematic of motorized wheelchair 600e is shown according to one embodiment. Motorized wheelchair 600e is similar to motorized wheelchair 600a of FIG. 6a, but includes navigation system 612 and has oxygen tank 620 coupled to the back of its seat. Navigation system 612 has anti-collision features as discussed herein. Oxygen tank 620 is shown as protruding beyond the rear boundary of contour 608. Sensors 604 provide sensor data to processing circuit 602, which detects the protruding oxygen tank 620 and compares it to contour 608. Processing circuit 602 calculates the amount l that oxygen tank 620 protruding and generates updated contour 616 to include the additional space occupied by the tank. The length of contour 608 is depicted as being extended along the entire rear span of motorized wheelchair 600e. Updated contour 614 also includes the areas of contour 608 that were unaffected by the protruding extremity. Updated contour 614 is provided to navigation system 612. Although depicted as an oxygen tank located on the rear of wheelchair 600e, oxygen tank 620 may be another object(s) (e.g., respiratory equipment, medical equipment, an I.V. drip bag stand, a flag, etc.). Further, oxygen tank 620 (and other objects) are not limited to a particular location, and are not limited to being attached to wheelchair 600e.

Figure 7:
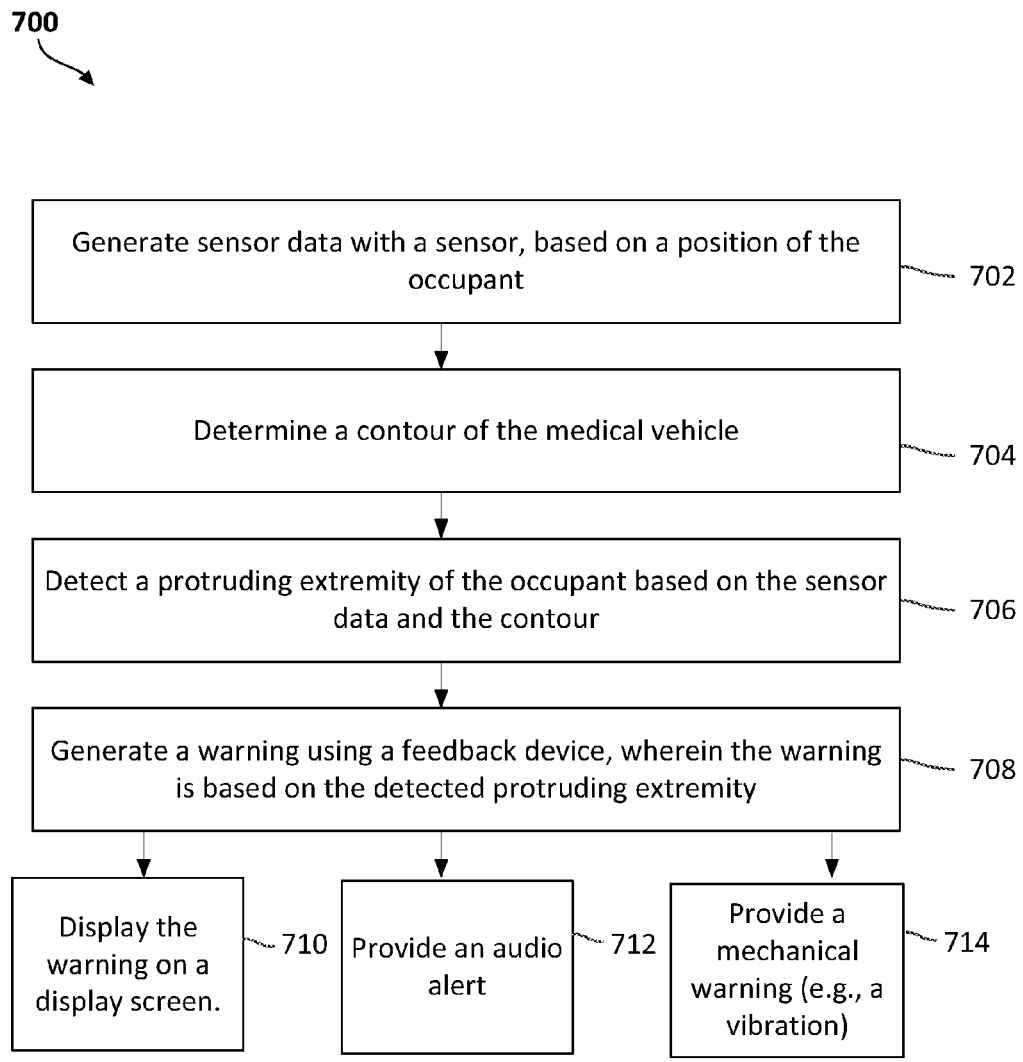
FIG. 7 is a flowchart of a process for warning of the protruding body parts of a medical vehicle occupant according to one embodiment.

Referring to FIG. 7, a flow diagram of a process 700 for warning of the protruding body parts of a medical vehicle occupant is shown, according to one embodiment. In alternative embodiments, fewer, additional, and/or different steps may be performed. Also, the use of a flow diagram is not meant to be limiting with respect to the order of steps performed. Sensor data is generated with a sensor, where the sensor data is generally based on a position of the occupant (702). The contour of the medical vehicle is determined (704). The contour may be determined based on the sensor data, or the contour may be predetermined and correspond to the particular medical vehicle. The sensor data and contour is analyzed to detect a protruding extremity of the occupant (706). If a protruding extremity is detected, then a warning is generated and output using a feedback device (708). The warning may include visual information displayed on a display screen (710), may include audio generated with a speaker (712), or may include mechanical feedback (714). The warning may be provided on a feedback device that is part of the medical vehicle, or may transmitted to a remote feedback device.

Figure 8:
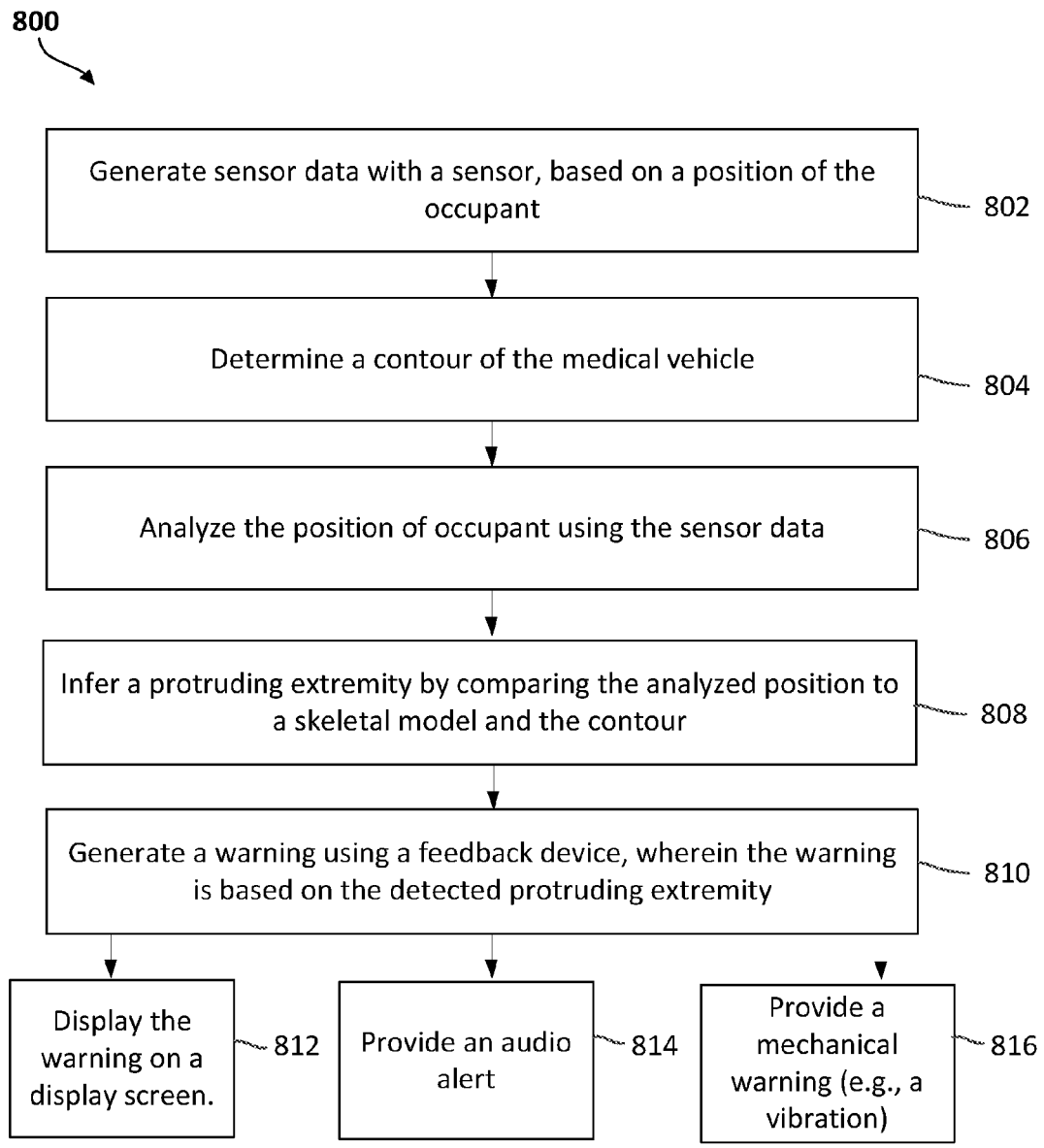
FIG. 8 is a flowchart of a process for warning of the protruding body parts of a medical vehicle occupant according to one embodiment.

Referring to FIG. 8, a flow diagram of a process 800 for warning of the protruding body parts of a medical vehicle occupant is shown, according to one embodiment. In alternative embodiments, fewer, additional, and/or different steps may be performed. Also, the use of a flow diagram is not meant to be limiting with respect to the order of steps performed. Sensor data is generated with a sensor (802), where the sensor data is generally based on a position of the occupant. The contour of the medical vehicle is determined (804). The position of the occupant in the medical vehicle is analyzed using on the sensor data (806). A protruding extremity is estimated or inferred by comparing the analyzed position to a skeletal model and the contour (808). If a protruding extremity is inferred, then a warning is generated and output using a feedback device (810). The warning may include visual information displayed on a display screen (812), may include audio generated with a speaker (814), or may include mechanical feedback (816).

Figure 9:
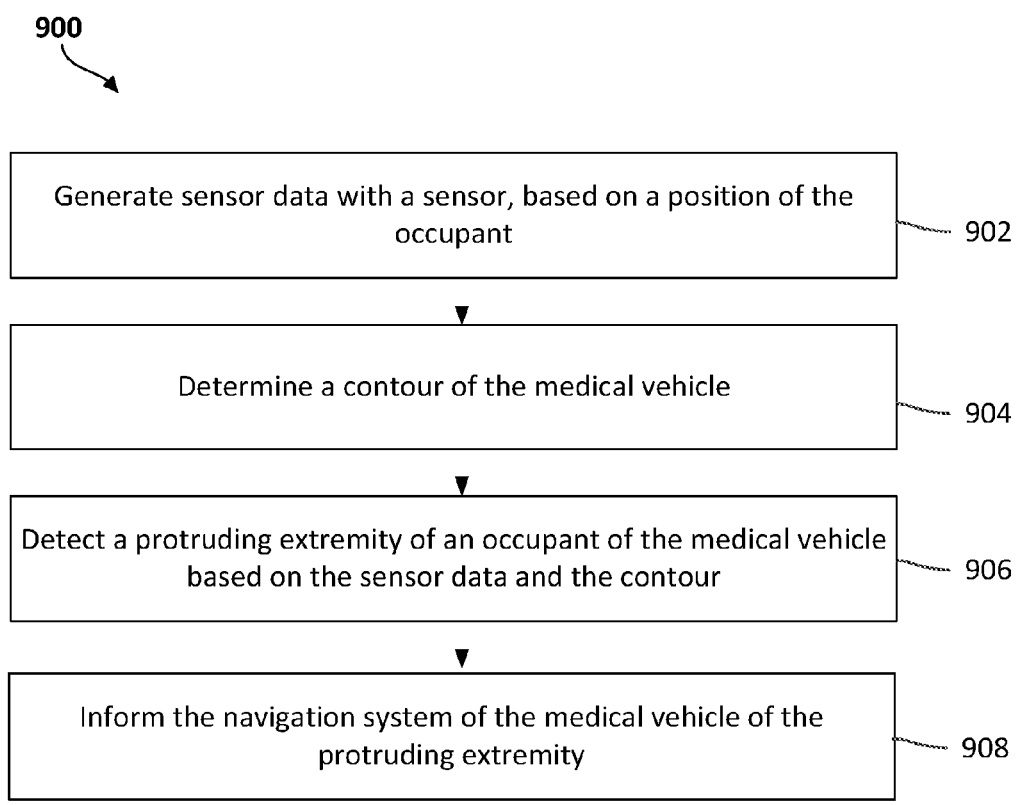
FIG. 9 is a flowchart of a process for notifying the navigation system of a medical vehicle of the protruding body parts of an occupant according to one embodiment.

Referring to FIG. 9, a flow diagram of a process 900 for notifying the navigation system of a medical vehicle of the protruding body parts of an occupant is shown, according to one embodiment. In alternative embodiments, fewer, additional, and/or different steps may be performed. Also, the use of a flow diagram is not meant to be limiting with respect to the order of steps performed. Sensor data is generated with a sensor, where the sensor data is generally based on a position of the occupant (902). The contour of the medical vehicle is determined (904). The sensor data and contour is analyzed to detect a protruding extremity of the occupant (906). If a protruding extremity is detected, then the navigation system of the medical vehicle is informed (908). Data may be formatted and sent to the navigation system according to the specifications of the particular medical vehicle.

Figure 10:
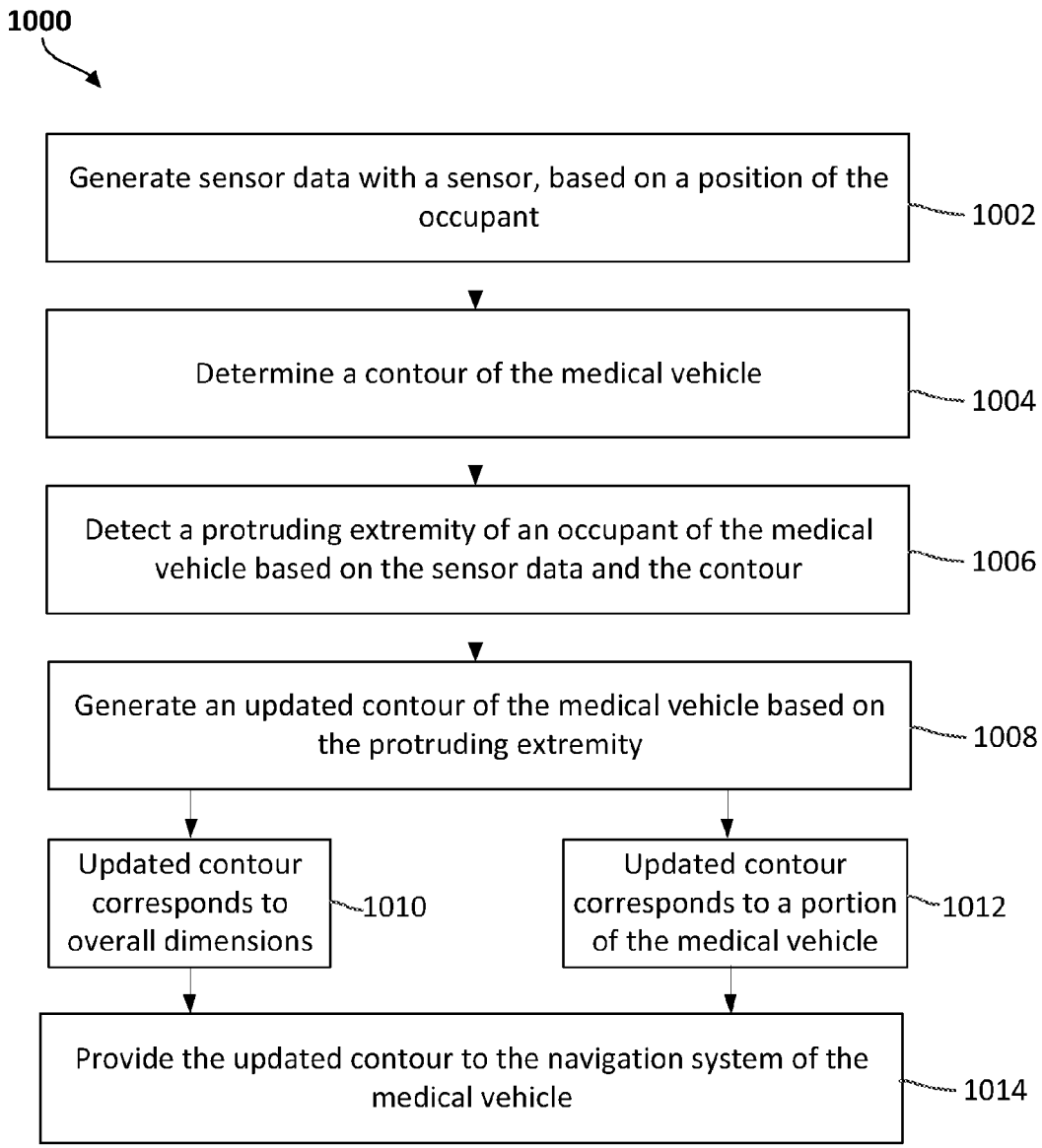
FIG. 10 is a flowchart of a process for notifying the navigation system of a medical vehicle of the protruding body parts of an occupant according to one embodiment.

Referring to FIG. 10, a flow diagram of a process 1000 for notifying the navigation system of a medical vehicle of the protruding body parts of an occupant is shown, according to one embodiment. In alternative embodiments, fewer, additional, and/or different steps may be performed. Also, the use of a flow diagram is not meant to be limiting with respect to the order of steps performed. Sensor data is generated with a sensor, where the sensor data is generally based on a position of the occupant (1002). The contour of the medical vehicle is determined (1004). The sensor data and contour is analyzed to detect a protruding extremity of the occupant (1006). If a protruding extremity is detected, an updated contour of the medical vehicle is generated based on the protruding extremity (1008). The updated contour may correspond to updated medical vehicle dimensions relating to the entire contour (e.g., the entire operating width of the medical vehicle is updated, etc) (1010), or the updated contour may be localized (e.g., an updated dimension near the location of the protruding extremity) (1012). The updated contour is provided to the navigation system of the medical vehicle (1014). Data may be formatted and sent to the navigation system according to the specifications of the particular medical vehicle.

Figure 11:
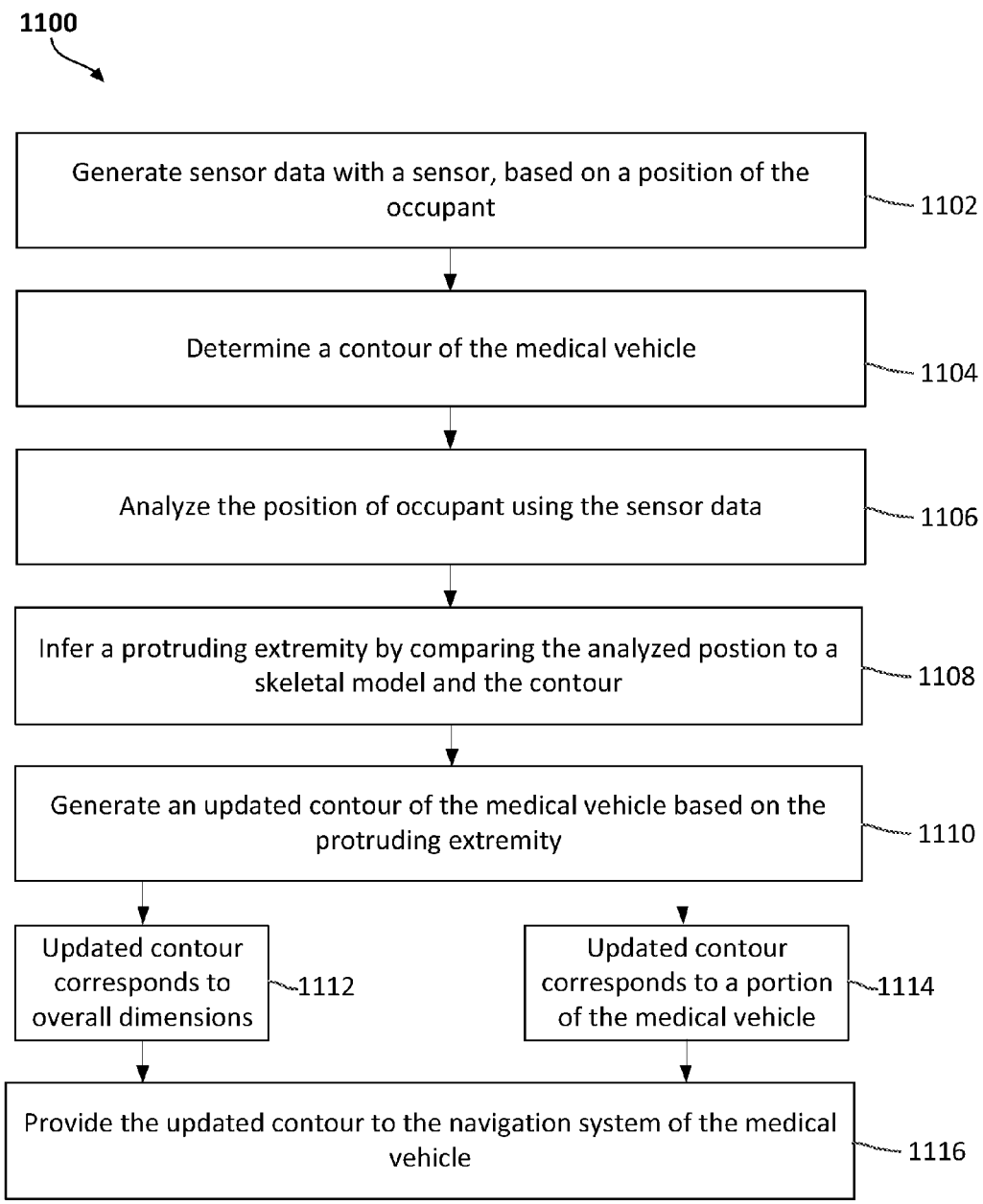
FIG. 11 is a flowchart of a process for notifying the navigation system of a medical vehicle of the protruding body parts of an occupant according to one embodiment.

Referring to FIG. 11, a flow diagram of a process 1100 for notifying the navigation system of a medical vehicle of the protruding body parts of an occupant is shown, according to one embodiment. In alternative embodiments, fewer, additional, and/or different steps may be performed. Also, the use of a flow diagram is not meant to be limiting with respect to the order of steps performed. Sensor data is generated with a sensor, where the sensor data is generally based on a position of the occupant (1102). The contour of the medical vehicle is determined (1104). The sensor data and contour is analyzed to detect a protruding extremity of the occupant (1106). A protruding extremity is inferred by comparing the analyzed position to a skeletal model and the contour (1108). If a protruding extremity is inferred, an updated contour of the medical vehicle is generated based on the protruding extremity (1110). The updated contour may correspond to overall updated medical vehicle dimensions (1112), or the updated contour may be localized to a particular portion of the medical vehicle (1114). The updated contour is provided to the navigation system of the medical vehicle (1116). Data may be formatted and sent to the navigation system according to the specifications of the particular medical vehicle.

Figure 12:
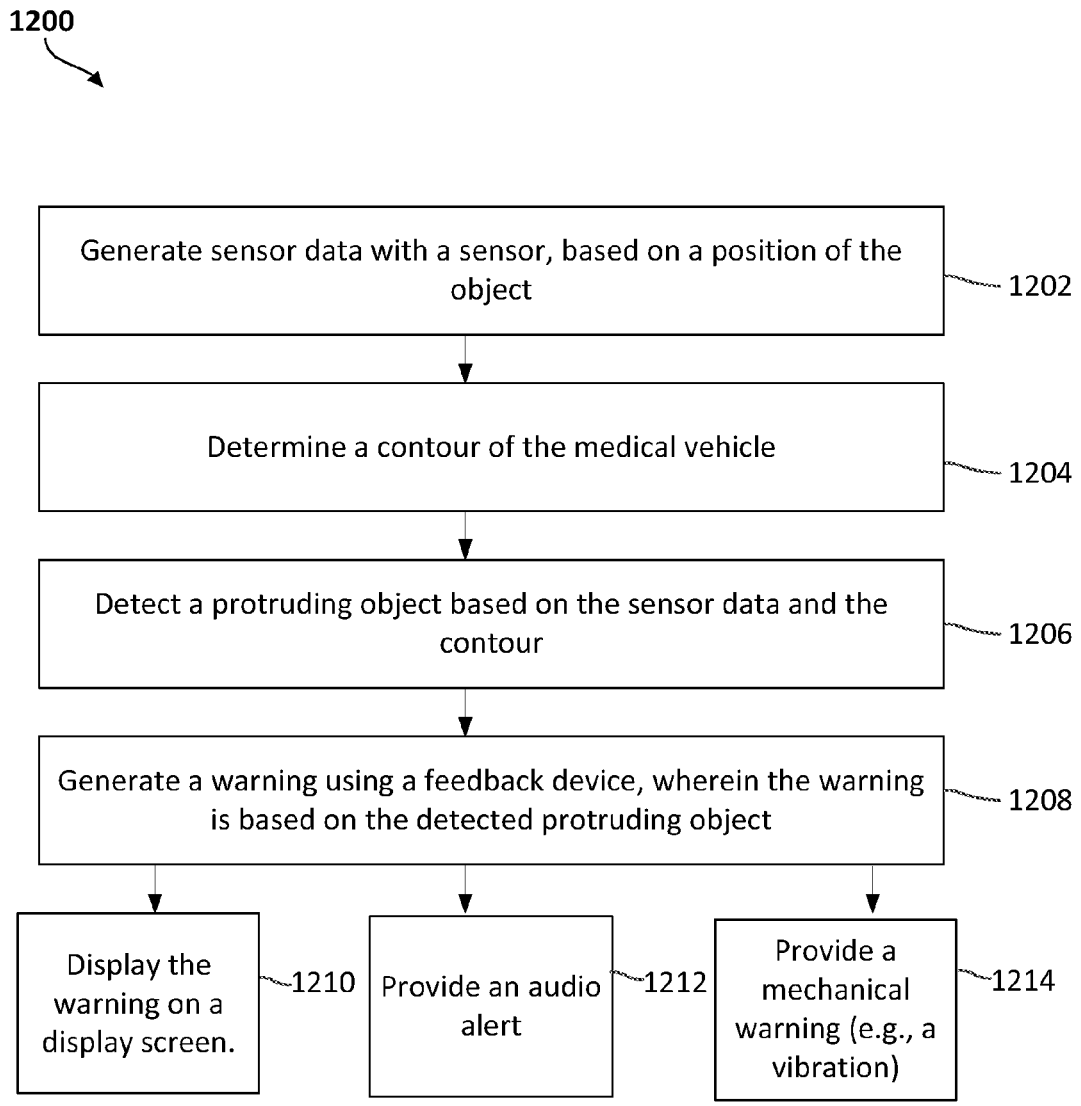
FIG. 12 is a flowchart of a process for warning of a protruding object of a medical vehicle according to one embodiment.

Referring to FIG. 12, a flow diagram of a process 1200 for warning of a protruding object of a medical vehicle is shown, according to one embodiment. In alternative embodiments, fewer, additional, and/or different steps may be performed. Also, the use of a flow diagram is not meant to be limiting with respect to the order of steps performed. Sensor data is generated with a sensor, where the sensor data is generally based on a position of the object (1202). The contour of the medical vehicle is determined (1204). The position of the object with respect to the medical vehicle is analyzed using on the sensor data. and a protruding object is detected (1206). If a protruding object is detected, then a warning is generated and output using a feedback device (1208). The warning may include visual information displayed on a display screen (1210), may include audio generated with a speaker (1212), or may include mechanical feedback (1214).

Figure 13:
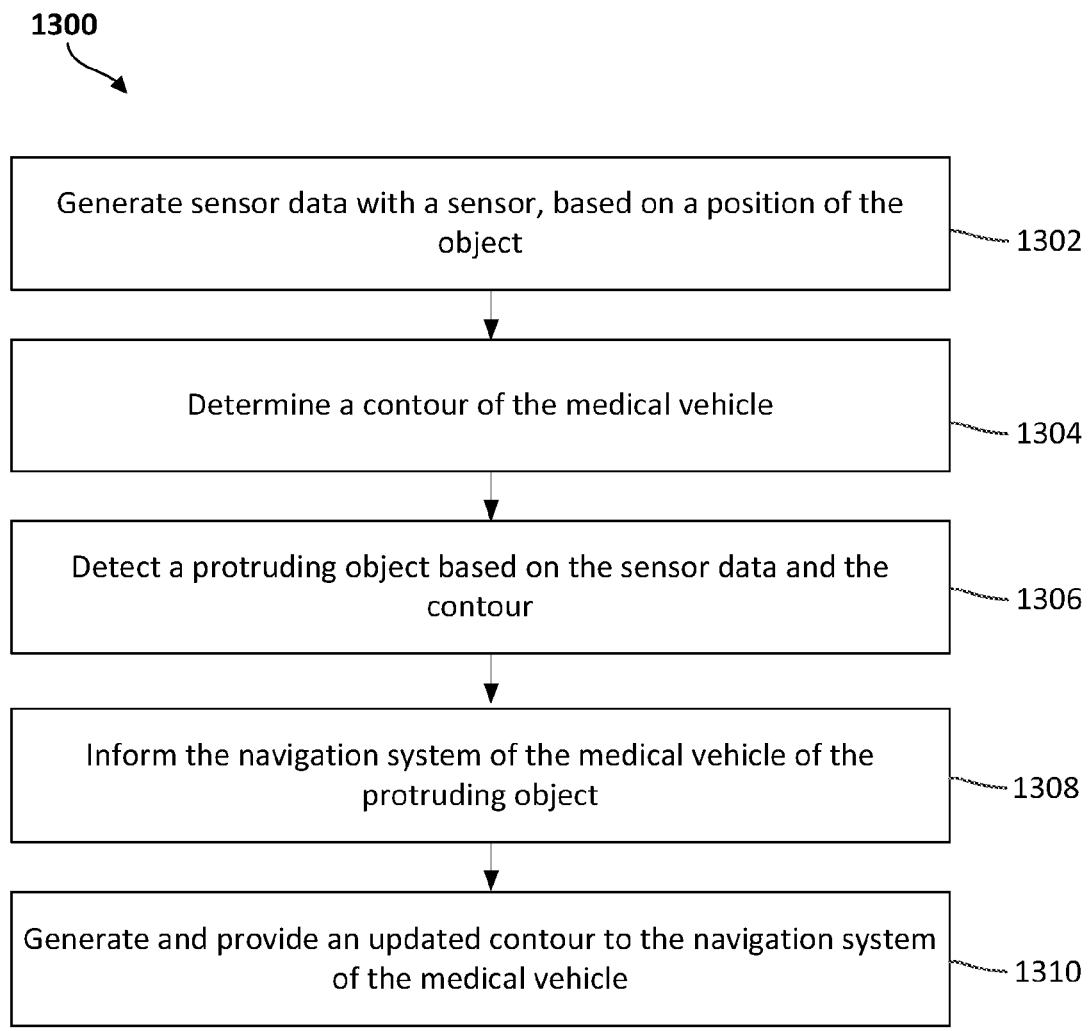
FIG. 13 is a flowchart of a process for notifying the navigation system of a medical vehicle of a protruding object according to one embodiment.

Referring to FIG. 13, a flow diagram of a process 1300 for notifying the navigation system of a medical vehicle of a protruding object is shown, according to one embodiment. In alternative embodiments, fewer, additional, and/or different steps may be performed. Also, the use of a flow diagram is not meant to be limiting with respect to the order of steps performed. Sensor data is generated with a sensor, where the sensor data is generally based on a position of the occupant (1302). The contour of the medical vehicle is determined (1304). The sensor data and contour is analyzed to detect a protruding object (1306). If a protruding object is detected, then the navigation system of the medical vehicle is informed (1308). The navigation system may also be provided an updated contour that takes into account the area of the protruding object (1310). Data may be formatted and sent to the navigation system according to the specifications of the particular medical vehicle.

The construction and arrangement of the systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for warning of a protruding body part of a medical vehicle occupant, comprising:
    a sensor configured to generate sensor data based on a position of the occupant;
    a feedback device; and
    a processing circuit configured to:
        determine a contour of the medical vehicle;
        detect a protruding extremity of the occupant that protrudes after the medical vehicle is in motion based on the sensor data and the contour, wherein detecting the protruding extremity includes determining a distance that the protruding extremity protrudes beyond a threshold distance beyond the contour of the medical vehicle and comparing the distance to the threshold distance; and
        generate a warning using the feedback device, wherein the warning is based on the comparison of the distance to the threshold distance.

2. The system of claim 1, wherein the sensor includes a camera, and wherein detecting the protruding extremity includes analyzing imaging data generated by the camera.

3. The system of claim 1, wherein the contour of the medical vehicle is determined based on at least one of the sensor data, a model of the medical vehicle, and a provided contour of the medical vehicle.

4. The system of claim 1, wherein detecting the protruding extremity is based on information related to skeletal anatomy, and wherein the skeletal anatomy is based on at least one of a model of the occupant and a model of an average human.

5. The system of claim 4, wherein detecting the protruding extremity comprises estimating the protruding extremity based on the skeletal anatomy and a non-protruding portion of the occupant.

6. The system of claim 5, wherein the sensor includes a pressure sensor configured to generate pressure data at a particular location on the medical vehicle, and wherein the processing circuit is further configured to detect the non-protruding portion of the occupant based on the pressure data.

7. The system of claim 5, wherein the sensor includes a capacitive sensor configured to generate touch data at a particular location on the medical vehicle, and wherein the processing circuit is further configured to detect the non-protruding portion of the occupant based on the touch data.

8. The system of claim 1, wherein the sensor includes a radar sensor.

9. The system of claim 1, wherein the sensor includes an RFID sensor, and wherein at least one RFID tag is coupled to the occupant.

10. The system of claim 9, wherein detecting the protruding extremity of the occupant is further based on a distance of the RFID tag from the RFID sensor.

11. The system of claim 1, wherein the sensor includes an optical sensor system coupled to the medical vehicle, and wherein the optical sensor system is configured to generate information related to objects crossing an optical path of the optical sensor system, and wherein detecting the protruding extremity of the occupant is further based on the information from the optical sensor system.

12. The system of claim 1, wherein the feedback device includes a speaker system, and wherein the warning includes audio played on the speaker system.

13. The system of claim 1, wherein the feedback device includes a display screen, and wherein the warning includes information displayed on the display screen.

14. The system of claim 1, wherein the feedback device includes a mechanical feedback system, and wherein the warning includes a vibration generated by the mechanical feedback system.

15. A system for notifying a navigation system of a medical vehicle of an occupant's protruding extremity, comprising:
a sensor configured to generate sensor data based on a position of the occupant; and
a processing circuit configured to:
determine a contour of the medical vehicle;
detect a protruding extremity of an occupant of the medical vehicle that protrudes after the medical vehicle is in motion, wherein detecting the protruding extremity is based on the sensor data and the contour, and wherein detecting the protruding extremity includes determining a distance that the protruding extremity protrudes beyond a threshold distance beyond the contour of the medical vehicle and comparing the distance to the threshold distance; and
notify the navigation system of the medical vehicle of the protruding extremity based on the comparison of the distance to the threshold distance.

16. The system of claim 15, wherein the processing circuit is further configured to generate an updated contour of the medical vehicle based on the protruding extremity.

17. The system of claim 16, wherein notifying the navigation system of the medical vehicle of the protruding extremity includes notifying the navigation system of the updated contour.

18. The system of claim 17, wherein the updated contour includes at least one of an extended contour corresponding to overall medical vehicle dimensions, a localized contour corresponding to a particular portion of the medical vehicle, and a model of the protruding extremity.

19. The system of claim 15, wherein the sensor includes a camera, and wherein detecting the protruding extremity includes analyzing imaging data generated by the camera.

20. The system of claim 15, wherein the contour of the medical vehicle is determined based on at least one of the sensor data, a model of the medical vehicle, and a provided contour of the medical vehicle.

21. The system of claim 15, wherein detecting the protruding extremity is based on information related to skeletal anatomy, and wherein the skeletal anatomy is based on at least one of a model of the occupant and a model of an average human.

22. The system of claim 21, wherein detecting the protruding extremity comprises estimating the protruding extremity based on the skeletal anatomy and a non-protruding portion of the occupant.

23. The system of claim 15, wherein the distance that the protruding extremity protrudes includes a percentage.

24. The system of claim 15, wherein the sensor includes a GPS sensor, and wherein the GPS sensor is configured to provide geospatial information related to the location of the medical vehicle, and wherein detecting the protruding extremity of the occupant is further based on the location of the medical vehicle.

25. The system of claim 15, wherein the sensor is integrated into the medical vehicle or integrated along a perimeter of the medical vehicle.

26. The system of claim 15, wherein the sensor is external to the medical vehicle.

27. The system of claim 15, wherein detecting the protruding extremity includes determining a particular type of the protruding extremity.

28. The system of claim 15, wherein the sensor is further configured to generate the sensor data based on a position of a protruding object, and wherein the processing circuit is further configured to:
detect the protruding object based on the sensor data and the contour; and
notify the navigation system of the medical vehicle of the protruding object.

29. A system for warning of a protruding object of a medical vehicle, comprising:
a sensor configured to generate sensor data based on a position of the object;
a feedback device; and
a processing circuit configured to:
determine a contour of the medical vehicle;
detect a protruding object that protrudes after the medical vehicle is in motion based on the sensor data and the contour, wherein detecting the protruding object includes a distance that the protruding object protrudes beyond a threshold distance beyond the contour of the medical vehicle; and
generate a warning using the feedback device, wherein the warning is based on the distance.

30. The system of claim 29, wherein the sensor includes a camera, and wherein detecting the protruding object includes analyzing imaging data generated by the camera.

31. The system of claim 29, wherein the contour of the medical vehicle is determined based on at least one of the sensor data, a model of the medical vehicle, and a provided contour of the medical vehicle.

32. The system of claim 29, wherein detecting the protruding object is based on a model of the object.

33. The system of claim 32, wherein detecting the protruding object comprises estimating the protruding object based on the model and a non-protruding portion of the object.

34. The system of claim 29, wherein the medical vehicle is at least one of a motorized wheelchair, a gurney, and a mobile bed.

35. The system of claim 29, wherein the feedback device includes a mechanical feedback system, and wherein the warning includes a vibration generated by the mechanical feedback system.

36. The system of claim 29, wherein detecting the protruding object includes determining a particular type of the protruding object.

37. The system of claim 29, wherein the object includes at least one of an oxygen tank, a walking aid, medical equipment, respiratory equipment, and a flag.

* * * * *